United States Patent
Chatenever et al.

(10) Patent No.: US 7,037,258 B2
(45) Date of Patent: May 2, 2006

(54) IMAGE ORIENTATION FOR ENDOSCOPIC VIDEO DISPLAYS

(75) Inventors: David Chatenever, Santa Barbara, CA (US); Daniel Mattsson-Boze, Sacramento, CA (US); Marc R. Amling, Santa Barbara, CA (US)

(73) Assignee: Karl Storz Imaging, Inc., Goleta, CA (US)

( * ) Notice: Subject to any disclaimer, the term of this patent is extended or adjusted under 35 U.S.C. 154(b) by 346 days.

(21) Appl. No.: 10/093,650

(22) Filed: Mar. 8, 2002

(65) Prior Publication Data

US 2002/0161280 A1    Oct. 31, 2002

Related U.S. Application Data

(63) Continuation-in-part of application No. 09/666,692, filed on Sep. 21, 2000, now Pat. No. 6,471,637.

(60) Provisional application No. 60/155,850, filed on Sep. 24, 1999.

(51) Int. Cl.
*A61B 1/045* (2006.01)

(52) U.S. Cl. .................. 600/109; 600/117; 600/173; 348/74

(58) Field of Classification Search ............... 600/117, 600/118, 109, 112, 173; 348/65, 73, 74, 348/208.1, 208.6, 208.16, 583
See application file for complete search history.

(56) References Cited

U.S. PATENT DOCUMENTS

| | | | | |
|---|---|---|---|---|
| 5,623,560 A | * | 4/1997 | Nakajima et al. | 382/295 |
| 5,661,519 A | * | 8/1997 | Franetzki | 348/66 |
| 5,677,763 A | | 10/1997 | Redmond | |
| 5,800,355 A | * | 9/1998 | Hasegawa | 600/436 |
| 5,885,218 A | * | 3/1999 | Teo et al. | 600/443 |
| 5,899,851 A | | 5/1999 | Koninckx | |
| 5,976,076 A | * | 11/1999 | Kolff et al. | 600/166 |
| 6,097,423 A | | 8/2000 | Mattsson-Boz et al. | |
| 6,178,271 B1 | * | 1/2001 | Maas, III | 382/294 |
| 6,464,631 B1 | * | 10/2002 | Girke et al. | 600/109 |
| 6,471,637 B1 | * | 10/2002 | Green et al. | 600/109 |
| 6,560,375 B1 | * | 5/2003 | Hathaway et al. | 382/295 |
| 2002/0045855 A1 | * | 4/2002 | Frassica | 604/109 |
| 2003/0016883 A1 | * | 1/2003 | Baron | 382/289 |

FOREIGN PATENT DOCUMENTS

| | | |
|---|---|---|
| JP | 6-269403 | 9/1994 |
| WO | WO 95/01749 | 1/1995 |

* cited by examiner

*Primary Examiner*—John P. Leubecker
(74) *Attorney, Agent, or Firm*—St. Onge Steward Johnston & Reens, LLC

(57) ABSTRACT

An apparatus and technique for compensating the display of an image obtained from a video camera system associated with an endoscope as it is moved through various orientations are described. The received optical image is converted to an electrical signal with an image sensor that can be a CCD or a CMOS detector. The endoscope video camera system has an inertial sensor to sense rotations of the received image about the optical axis of the endoscope and the sensor's output signals are used to rotate either the image or the image sensor. In case of rotation of the image sensor the rotation sensor can be a gyroscope or a pair of accelerometers. In case of a rotation of the image obtained with the image sensor the inertial sensor, which can be an accelerometer or a gyroscope, the image is rotated within a microprocessor for subsequent viewing on a video display.

2 Claims, 18 Drawing Sheets

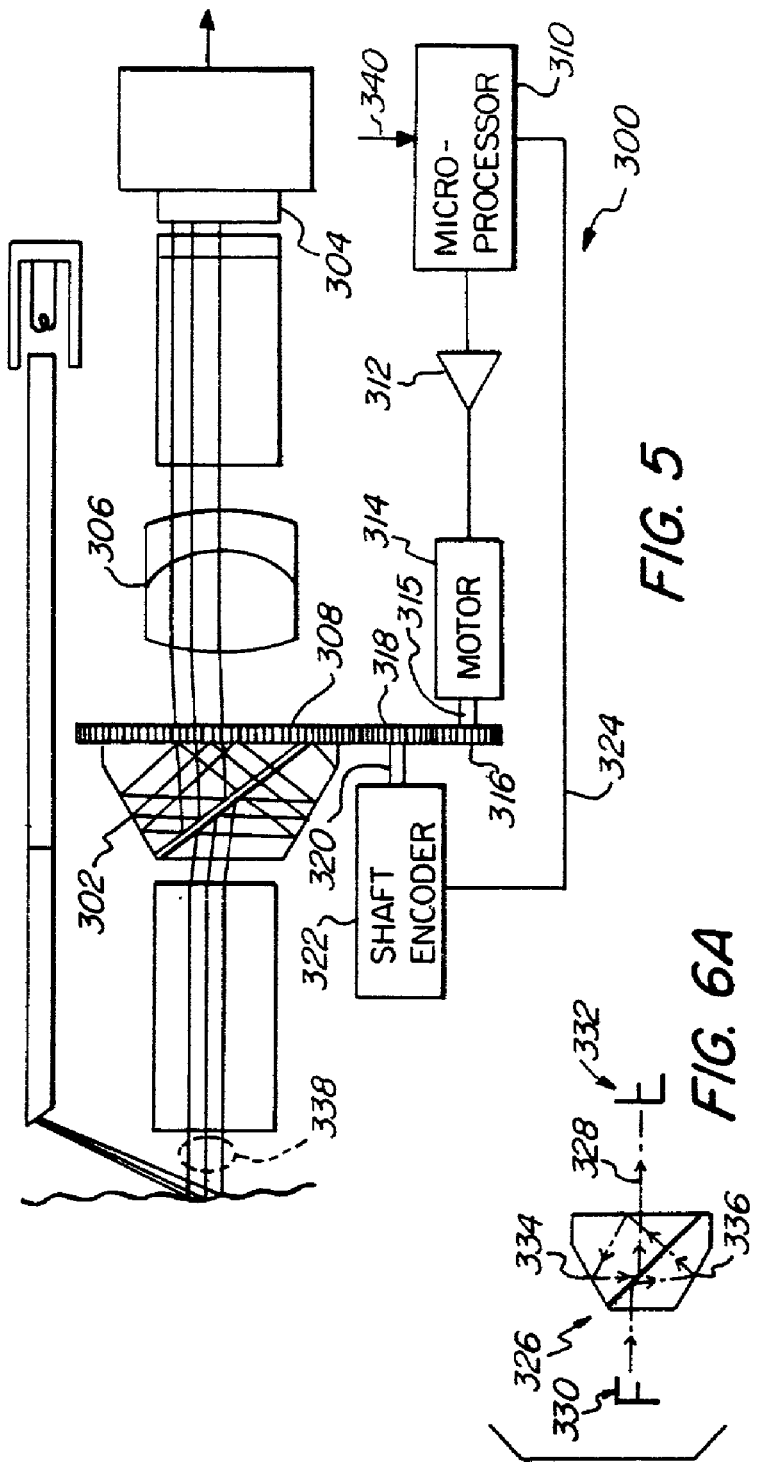

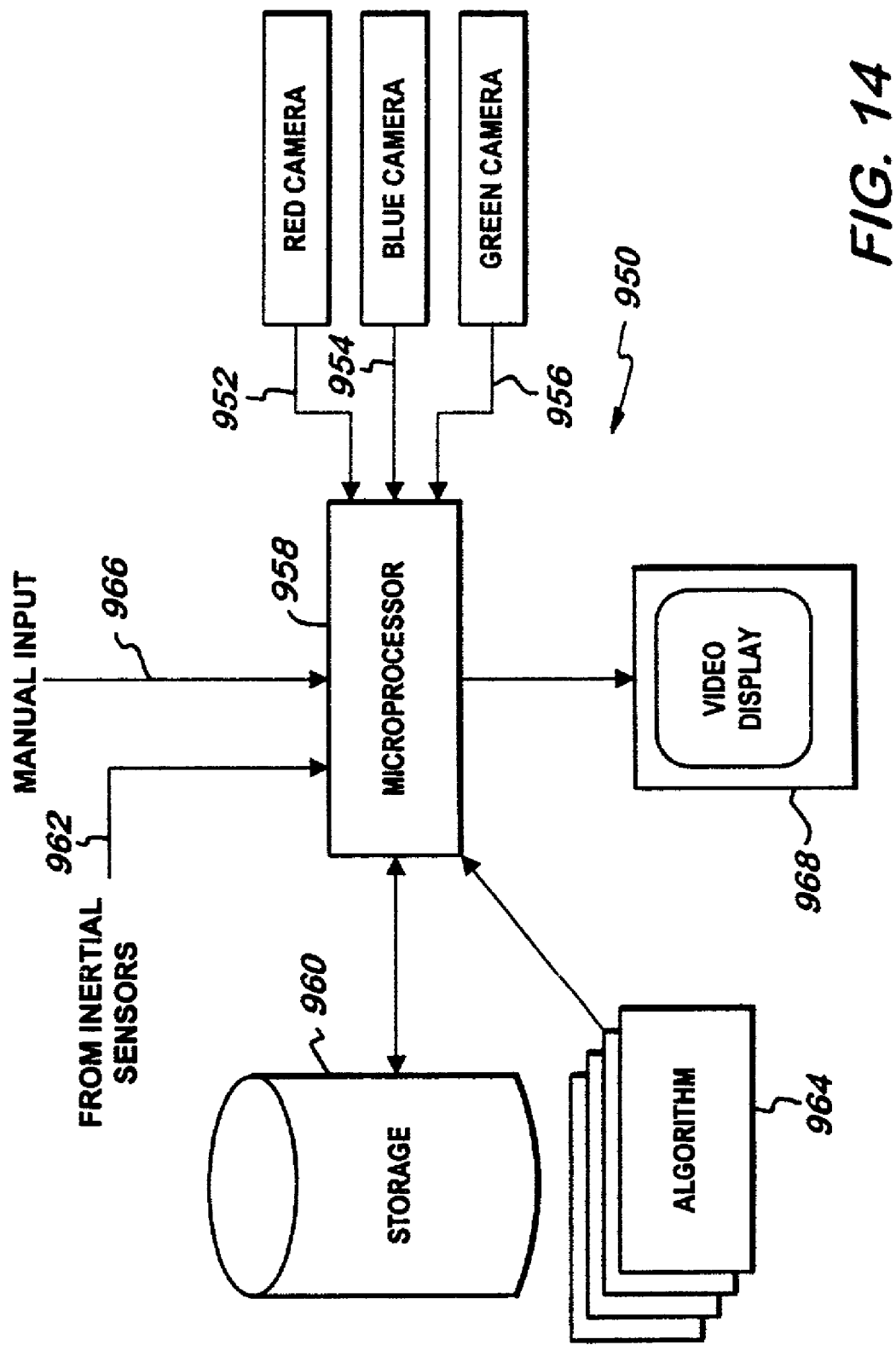

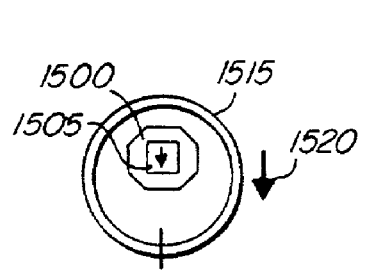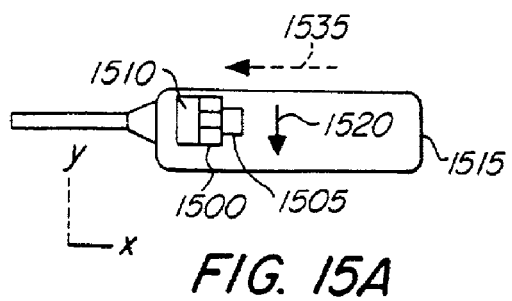
FIG. 15B  FIG. 15A
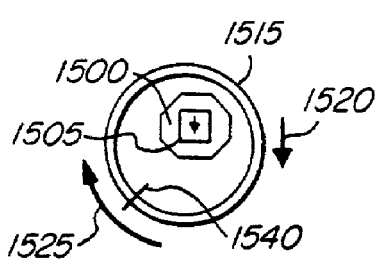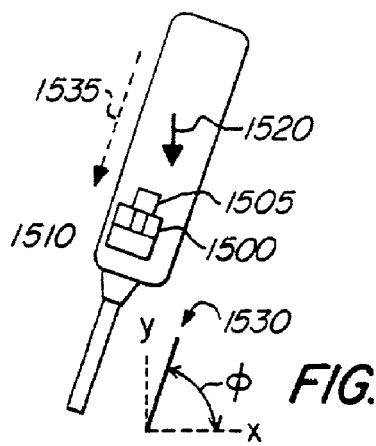
FIG. 15C  FIG. 15D
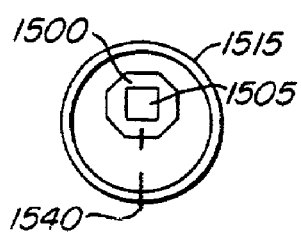
FIG. 15F
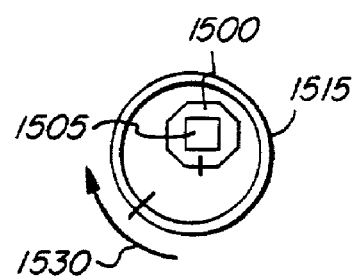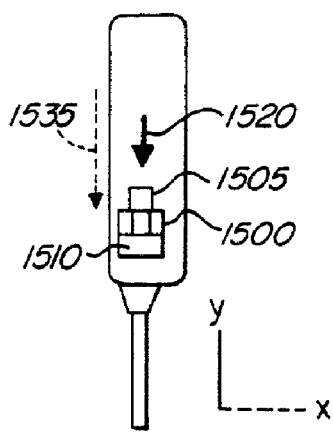
FIG. 15G  FIG. 15E

IMAGE ORIENTATION FOR ENDOSCOPIC VIDEO DISPLAYS

CROSS-REFERENCE TO PRIOR APPLICATIONS

This is a continuation in part of U.S. patent application Ser. No. 09/666,692 filed Sep. 21, 2000, now U.S. Pat. No. 6,471,637, for Stabilized Endoscope Image Orientation, which claims the benefit of, under 35 U.S.C. 119(e), provisional patent application Ser. No. 60/155,850 of Chatenever filed Sep. 24, 1999.

FIELD OF THE INVENTION

This invention relates generally to video displays of images obtained from an endoscope. Specifically this invention relates to a re-orientation of an image as viewed on a display screen to present the image in a preferred relationship to the viewer's reference frame. More specifically this invention relates to inertial sensor techniques for re-orienting such image as it is obtained with an endoscope used to view a body part through an opening in a body.

BACKGROUND OF THE INVENTION

An endoscope is an elongated tubular structure that is inserted into body cavities to examine them. The endoscope includes a telescope with an objective lens at its distal end. The telescope includes an image-forwarding system. In rigid endoscopes it may be a series of spaced-apart lenses. In flexible endoscopes it may be a bundle of tiny optical fibers assembled coherently to forward the image. This invention is applicable to both types of image forwarding systems.

At the proximal end of the image-forwarding system is an ocular lens, which creates a virtual image for direct human visualization. Often, a camera means such as a charge coupled device (CCD) chip, is mounted to the endoscope. It receives the image and produces a signal for a video display. A CCD is a semiconductor component that is used to build light-sensitive electronic devices such as cameras and image scanners. Each CCD chip consists of an array of light-sensitive photocells that produce an analog output proportional to the intensity of the incident light.

While surgeons can, and often do, look directly into the endoscope through an ocular lens, it is more common for them to use an attached video camera and observe an image on a video screen. In a surgical or diagnostic procedure, the surgeon uses the endoscope. He may tilt it, push it in, pull it out, and also rotate it around its mechanical axis. As these manipulations occur to an endoscope with an attached video camera, the camera faithfully relates what it sees, with its own upright axis displayed as the upright axis of the image on the display. This means that if the camera is rigidly fixed to the endoscope, and the endoscope-camera is moved to view a body region by, for example, rotating the instrument, the displayed image on the monitor will move proportionately and in the opposite direction to that of the endoscope camera. For example, a clockwise rotation of the endoscope-camera, or the distal end of the endoscope, through an angle of 45 degrees will still produce an upright image on the display. But in the reference frame of the user, who caused the clockwise rotation of the instrument, the image should be viewed as if it had been rotated clockwise. Since the image remains upright, it appears to the user as if there was a counterclockwise rotation of the image on the monitor through an angle of 45 degrees.

That is the very problem. When the image is displayed on the screen and the endoscope is rotated around its axis, it is as though the surgeon must tilt his head to follow it. However, the surgeon is standing up, and the rotating image is distracting to him. What he really wants to see on the screen is an image that is oriented the same as he would see it if he were inside, standing up, with the same upright orientation. Stated otherwise, he would prefer to see what he would see if he were looking directly into the endoscope, instead of viewing a screen. This is impossible when the camera is fixed to the telescope and rotates with it, while the surgeon does not.

In a conventional endoscope and camera arrangement, the camera is usually detachably and rotatably connected to the endoscope. In this arrangement the rotated image on the monitor screen can be righted by manually counter-rotating only the camera such that its orientation is upright. Alternatively, one can avoid this rotated image condition by holding the camera in its upright position and rotating only the endoscope.

Suggestions have been made to decouple the camera from the telescope so the camera can rotate independently of it, using a pendulum to seek the vertical. This seemingly sensible approach runs afoul of conditions imposed by the use of the instrument. Endoscopes are used in close quarters, and their proximal ends must be kept as small and uncluttered as possible. Physical interference with surroundings and with the surgeon's hands must be eliminated or greatly minimized. However, a pendulum to be useful must have a substantial mass and a substantial arc to work through, requiring enlargement of the instrument. Furthermore, when the endoscope is tilted, the axis of rotation of the pendulum is no longer horizontal. Now there must be bearings to support the pendulum, and the component of the force of gravity acting on the pendulum is reduced. Even worse, when the slope is very steep, a mechanical pendulum may not receive a sufficient force to seek the vertical.

Sometimes, however, there may be reasons to attach the endoscope such that it cannot rotate with respect to the camera. Or, alternatively, it may be desirable to embed the video camera within the endoscope housing. In these circumstances it is not possible to manually rotate the camera with respect to the endoscope, so some other means is necessary to right the displayed image. Furthermore, it is desirable to have this image rotation occur automatically so that, regardless of the physical orientation of the endoscope-camera in space, the displayed image of an object will always be correctly oriented with respect to the viewer's reference frame.

In addition to the rotation effects, a further perspective distortion occurs from the difference between viewing the objects directly in three-dimensions with the eyes and on a two-dimensional camera image. This perspective distortion occurs when the endoscope/camera combination views an object from a vantage point that is above (or below) and to the side, relative to the surgeon's direct "line-of-sight." The vanishing point of the perspective view is on the side of the rendered object furthest from the endoscope's vantage point. This results in objects closest to the endoscope end appearing disproportionately large and also results in horizontal lines appearing tilted in the display.

U.S. Patent Application Ser. No. 60/155,850 of Chatenever and U.S. Pat. No. 6,097,423 disclose a device for correcting for the rotation of the endoscope's distal end. That invention uses a single accelerometer to determine the angular displacement of the endoscope using the direction of gravity, as sensed with the accelerometer, for a vertical reference and as described in the '423 patent rotates a CCD image sensor aligned with the optical axis of the endoscope so as to maintain a desired orientation of a display of the image on a monitor.

U.S. Pat. No. 5,881,321 to Kivolowitz, Mar. 9, 1999, discloses a system for using absolute position of a hand-held camera by use of inertial sensors incorporated into the structure of the camera to detect the movement of the camera along three orthogonal axes, as well as angular rotation around the three axes. This device uses a wireless communication device for transmitting the position data and remote processing to alter the generation of images. The wireless communication approach, while appropriate for the larger video or motion picture camera contemplated therein, adds batteries and considerable circuitry and therefore size which is unavailable in the tight quarters required in an endoscope. Additionally, no provision is disclosed for mechanical alignment of the image prior to the processing for display.

BRIEF DESCRIPTION OF THE INVENTION

In accordance with one aspect of the current invention, as an endoscope is moved or rotated during usage, the disclosed invention provides signals for an image display that is rotated to compensate for the movement or rotation of the endoscope. In this manner the displayed image does not rotate as the surgeon rotates the endoscope.

Inertial sensors, such as accelerometers or gyroscopes, are employed to provide a signal proportional to the angular rotation of the endoscope. A microprocessor or other electronic circuitry calculates a compensating rotational signal from the proportional signal. The compensating rotational signal is used to re-orient the received image.

In this aspect of the invention the image received from the endoscope distal end may be rotated in three ways: physical rotation of the image sensor; optical rotation of the received image prior to incidence upon the image sensor, and; electronic rotation of the image sensor signals. Physical rotation of the image sensor is accomplished by having the sensor rotatably attached to the endoscope. The compensating rotational signal drives a motor or similar device to rotate the image sensor in a direction opposite to the rotation of the endoscope.

Optical rotation of the received image is accomplished by interposing an optical device between the image received from the endoscope distal end and the image sensor. The optical device is of such a construction that an image viewed through the device appears to rotate as the device is rotated. Certain inversion prisms such as the Pechan prism Dove prism, Taylor and compact prisms have this characteristic. The compensating rotational signal drives a motor or similar device to rotate the optical device in a direction so as to compensate for the rotation of the endoscope thereby rotating the image that is incident upon the image sensor.

In another aspect of the present invention, the view presented by the video display can store a preset angle to accommodate what the surgeon needs to see along the axis of the instruments while conducting his procedure within the body cavity. The compensating rotational signal is modified to provide an image orientation that is preferred by the surgeon. This user supplied value is employed by the microprocessor as an offset to the display image rotation provided by the inertial sensors. This allows the surgeon to have the displayed image rotated to any desired orientation and have the invention maintain the image in that orientation.

BRIEF DESCRIPTION OF THE DRAWINGS

FIG. 5 is a schematic diagram illustrating an apparatus and control system of an alternative embodiment of the invention;

FIGS. 6A and 6B are phasor diagrams of an image incident on a Pechan prism;

FIG. 14 is a schematic diagram of a control for the fifth embodiment.

FIG. 15A is side schematic view of a horizontally held endoscope with camera head and image sensor;

FIG. 15B is a schematic cross-sectional representational view of the image sensor in the endoscope in FIG. 15a with the camera having a first orientation;

FIG. 15C is a schematic cross-sectional representational view of the image sensor in the endoscope in FIG. 15a with the camera having been rotated over an angle of about 45 degrees;

FIG. 15D is a side schematic view of the camera after it has been partially rotated towards the local vertical, the Y axis;

FIG. 15E is a side schematic view of the camera of FIG. 15a after the camera has been rotated fully to the local vertical Y axis;

FIG. 15F is a schematic cross-sectional representational view of the image sensor in the camera of FIG. 15a at a time when a correction for gyro drift is made;

FIG. 15G is a schematic cross-sectional representational view of the image sensor in the camera of FIG. 15a at a time when gyroscopic control is enabled;

DETAILED DESCRIPTION OF THE INVENTION

Figure 1:
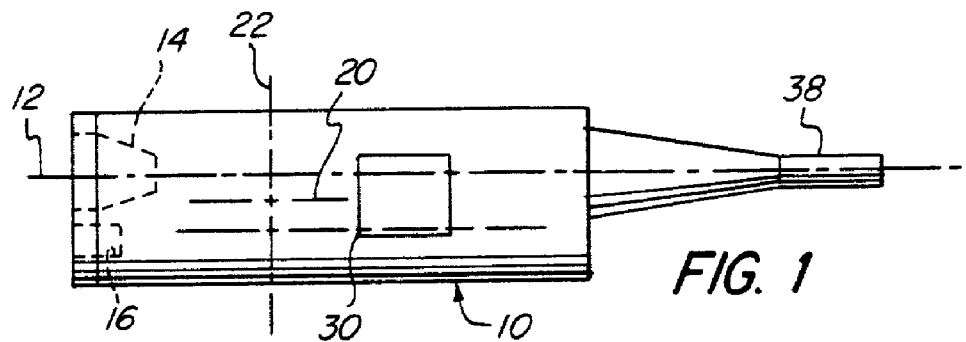
FIG. 1 is a side view of a camera for use with an endoscope in accordance with this invention.

With reference to FIG. 1, frame 10 has two receptacles 14 and 16 adapted to receive an endoscope (not shown), which may be releasable or permanently attached to the frame. A light source provides illumination through receptacle 16 to the proximal end of the endoscope. The light is reflected off the walls of an internal body cavity to an image forwarding system of the endoscope at the distal end and the light image received at receptacle 14 about a central optical axis 12. The light image received may be directly, or through a series prisms and lenses, made incident upon an image sensor 30 disposed within the frame 10. The image sensor 30 output image signals are provided through an exit cable 38 for further processing and display on a video monitor. Frame 10, in its upright position, has a lateral horizontal axis 20 and an upright axis 22 that is vertical in the gravitational field. Axes 20 and 22 are normal to each other. U.S. Patent Application Ser. No. 60/155,850 of Chatenever has a more complete description of an endoscope and is included herein by reference thereto.

In this aspect of the present invention, applying an automatic compensating angular rotation to the video display image minimizes distracting effects of endoscope rotation on the video display. First the angular orientation of the image sensor is determined. Second, this angular change is used to re-orient, or compensate, the video display image thereby stabilizing the display image.

Here it will be noted that the endoscope when in use will have freedom to tilt in all directions. When the endoscope is rotated around its axis the image displayed on the video display will also rotate. This motion is distracting to the surgeon. Worse, when the endoscope rotates clockwise the video display image will rotate counterclockwise. This result is described herein below with respect to FIGS. 2A and 2B.

Figure 2A:
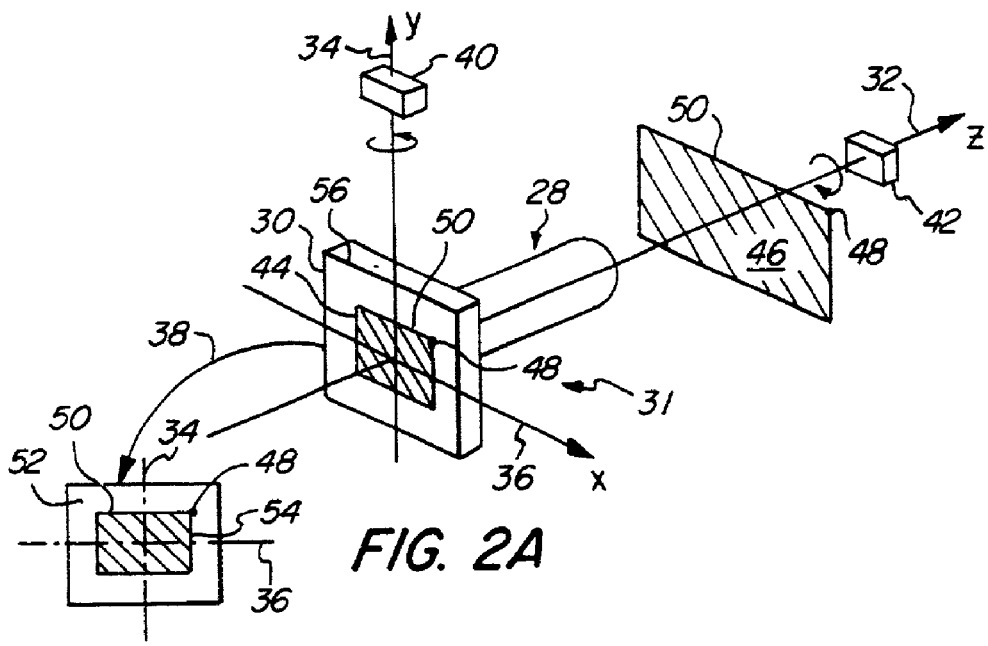
FIGS. 2A and 2B are schematic views of the image orientation in accordance with the invention.
Figure 2B:
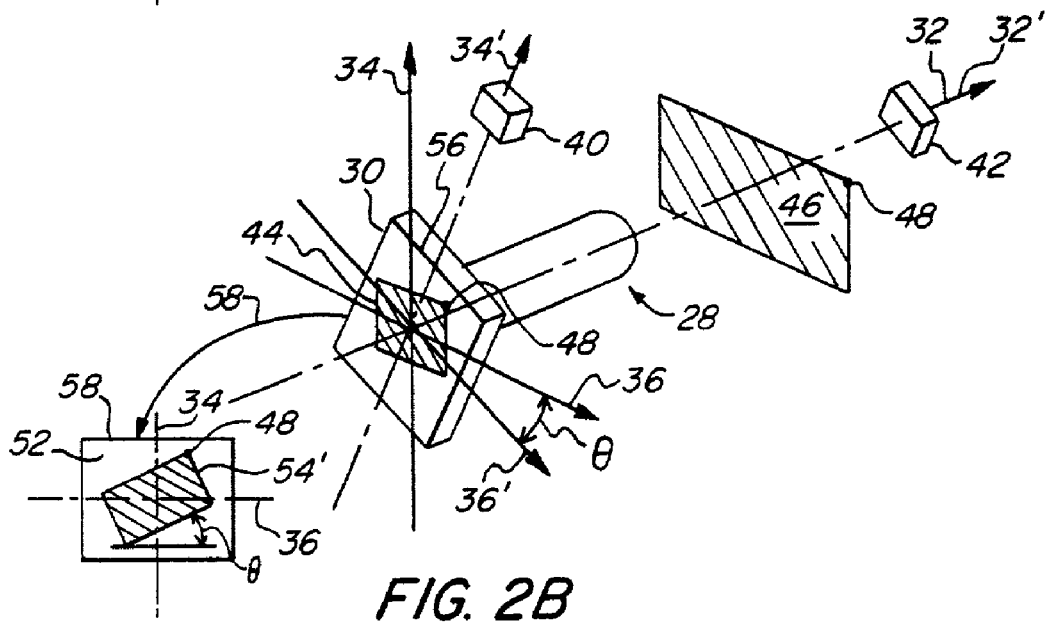

FIGS. 2A and 2B illustrate the effects of endoscope 28 rotation on the video display. Referring to FIG. 2A, the orientation of an image sensor 30 is described by a three orthogonal axis system 31: a z-axis 32 is defined as coincident with the optical axis of image sensor, a y-axis 34 is coincident with the direction of gravity, and an x-axis 36 is orthogonal to a plane defined by x- and z-axes. Image sensor 30 may be a CCD or similar optically sensitive device or system. The image sensor 30 may rotate in any of the three planes determined by orthogonal axis system 31. Deviation in the x-y plane is defined as "image rotation;" deviations in the y-z together with deviations in the x-z plane result in image obliqueness described further herein below with respect to FIG. 9.

FIG. 2A illustrates an endoscope 28 with image sensor 30 capturing an image 46. For illustrative purposes, both image sensor 30 and image 46 of an object are rectangles orthogonal in the x,y plane. A sensor projection 44 depicts image 46 as projected onto image sensor 30 and its orthogonal axis system 31. The image sensor 30 outputs, on a line 38, the electronic representation of image 46 to a video display 52.

Video display 52 has vertical axis 34 and horizontal axis 36 respectively parallel to y-axis 34 and x-axis 36. Display image 54 on video display 52 is representative of image 46 as viewed by image sensor 30 and presents a rectangle. Note the position of image 46 corner 48 as projected onto image sensor 30 and displayed on video display 52. Corner 48 appears on a horizontal line 50 of image 46 closest to the top edge 56 of image sensor 30.

FIG. 2B illustrates endoscope 28 with image sensor 30 rotated through an angle theta, $\Theta$. Image 46 has not rotated so projection 44 onto orthogonal axis system 31 is the same as in FIG. 2A with corner 48 located as before. Since image sensor 30 has rotated, corner 48 is located closer to image sensor 30 top edge 56. Therefore, corner 48 is displayed as closer to a top edge 58 of display 52. It is now seen that while image sensor 30 rotates clockwise through angle $\Theta$, as defined between the axes 36, 36', a displayed image 54' has rotated counterclockwise through the same angle. The changed orientation of the orthogonal axis system 31 is shown with reference to the orientation of its axes as identified by numerals 32', 34' and 36'.

In this aspect of the present invention, a plurality of inertial sensors 40 and 42 are used to monitor the angular orientation of image sensor 30 with respect to orthogonal axis system 31. For the purposes of illustration, these sensors are shown as a y-sensor 40, and a z-sensor 42. The usage of two types of inertial sensors is described: accelerometers used as gravity detectors and gyroscopes used as angular displacement detectors. Once the angular orientation of image sensor 30 is determined, the display image 54' may be rotated an essentially equivalent amount in a compensating direction.

Figure 3:
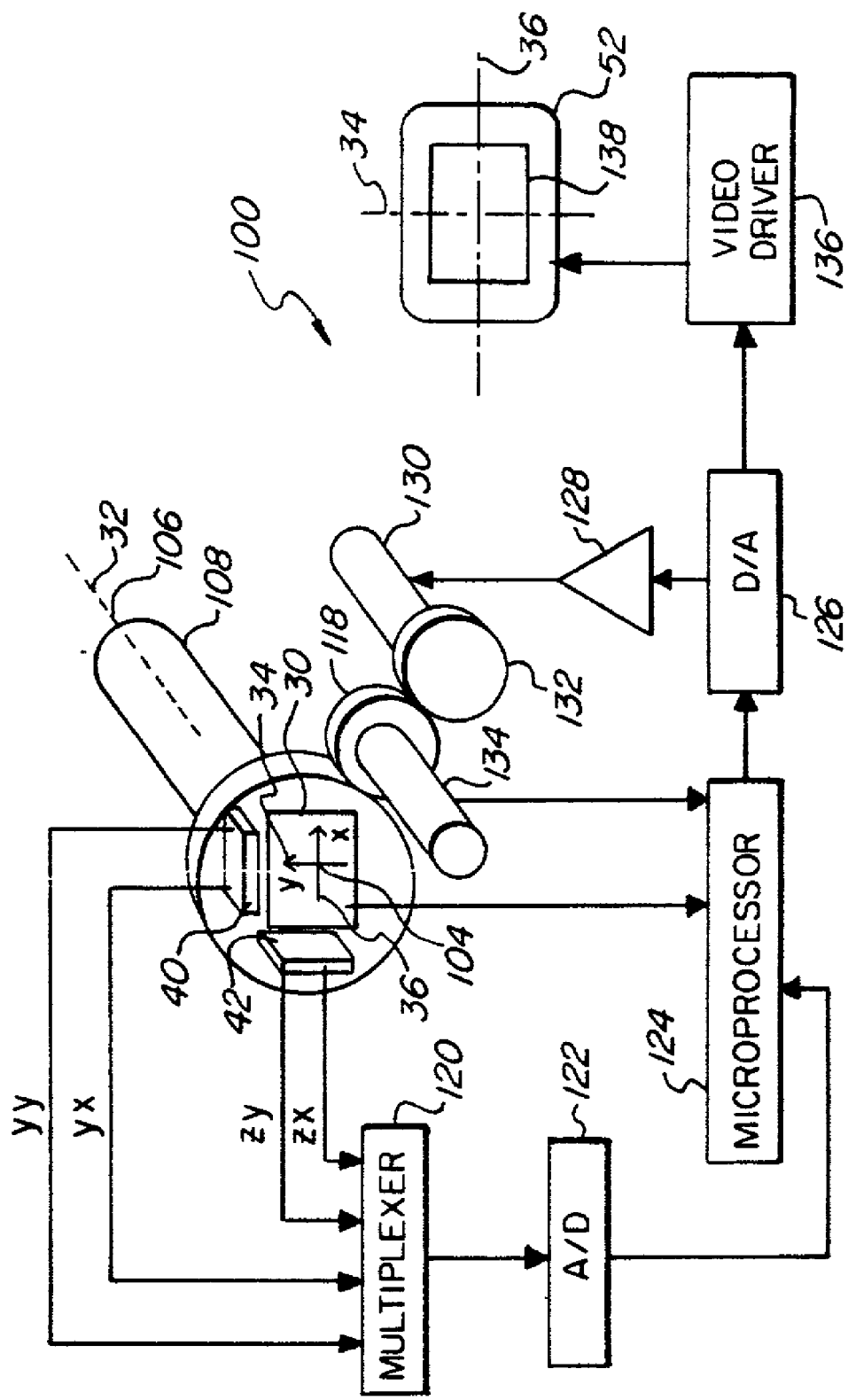
FIG. 3 is a schematic diagram illustrating the apparatus and control system of a first embodiment of the invention.

In a first embodiment shown in FIG. 3, two accelerometers 40, 42 are used to determine angular rotation of image sensor 30 about its optical z-axis 32. When in use, the endoscope will have freedom to tilt in all directions so that the accelerometer will often be responding to a component of vertical gravitational force that is considerably less than its maximum value. In some instances the camera enters the anatomy at an angle that is so extreme that it becomes difficult to determine, by use of a single gravity sensor, in which direction or how much of an automatic angular compensation is required. For example, when z-axis 32 is depressed 60 degrees, the vertical component of gravity to which first accelerometer 42 refers while keeping the image upright is much less than maximum gravity force. The second accelerometer 40 is oriented so that the vertical component of gravity upon it increases as z-axis 32 is depressed. Thus the angular offset required can be derived from the two accelerometers 40 and 42. It is an advantage of the present invention that it can thereby respond properly over different orientations of endoscope 28.

In an alternative embodiment, a single rate gyroscope (gyro) can be used as the inertial sensor 42 in FIG. 2. This embodiment obviates the need for an additional sensor 40. The gyro output is used to determine the offsetting rotational requirement. A gyro creates a signal representative of a force proportional to the angular displacement relative to its axis of rotation. The gyro does not produce such a signal if the axis of rotation is merely translated. For example, a gyro having an axis of rotation parallel to the x-axis will produce a signal indicative of a force in response to an attempt to angularly displace the axis around either the y or z orthogonal directions. Hence, a gyro in this example provides signal indicative of a force proportional to the angular displacement in the y-z plane or rotation about the x axis.

It is to be observed that in either the two-accelerometer or the single gyro embodiment, a signal is developed that represents the angular rotation of image sensor. Usage of that signal to provide angular rotation compensation of the video display image may be achieved through alternative embodiments of the present invention and it is to these alternative embodiments that we now turn our attention.

FIG. 3 illustrates an apparatus 100 to automatically compensate for various angular orientations of an endoscope optical axis 106 according to the present invention. An image sensor 30 is rotatably mounted to the endoscope frame (not shown). Image sensor 30 center point 104 may be located on optical axis 106 of the image forwarding system of the endoscope or optical axis 106 may be redirected by prisms through center point 104. Image sensor 30 is rotatable around its center point 104. Image sensor 30 has its own lateral axis 36 and upright axis 34. Upright axis 34 is aligned with the direction of gravity.

A first inertial sensor 40 for sensing rotation of the camera around the y-axis, i.e. rotation in the x-z plane, is rotatably mounted to the frame. In a similar manner a second inertial sensor 42 for sensing rotation of the camera around the z-axis 32, i.e. rotation in the x,y plane, may be rotatably mounted to the frame. Both sensors 40 and 42 are in a fixed spatial relationship and rotate with image sensor 30. Most conveniently, the sensor(s) is directly bonded to image sensor 30. A rotational driver 118 can serve to rotate inertial sensors 40, 42 and image sensor 30.

In the case where inertial sensors 40 and 42 are accelerometers, two signals for each sensor corresponding to y-axis and z-axis accelerometer outputs, respectively, are applied through a multiplexer 120 to an A/D converter 122. The resulting digital signals are applied to a microprocessor 124 together with the output signals from image sensor 30. Microprocessor 120 analyzes the y and z signals and derives an angular rotation compensating signal that is supplied to a D/A converter 126. The output of D/A converter 126 is applied through an amplifier 128 to drive a motor 130. Motor 130 is bi-directional to rotate rotational driver 118 that in turn journals image sensor 30 and accelerometers 40 and 42.

A motor output gear or driver 132 is affixed to the output shaft of motor 130. Rotation of motor 130 rotates motor output gear 132 which in turn rotates a gear or rotational driver 118. The gear 118 is fixed on the shaft of an encoder 134. The encoder can also be located in the motor 130. Encoder 134 applies a servo signal feedback to microprocessor 124. Microprocessor 124 interprets the feedback signal to determine whether further accelerometer rotation is required. As a result, image sensor 30 is rotated about its optical axis so that upright axis 34 is re-aligned with the direction of gravity.

Alternatively, a rate gyro can be used to replace both accelerometers 40 and 42. Unlike an accelerometer, a gyro will require initialization in order to align its axis of rotation with either the direction of gravity or lateral axis 36 of image sensor 30. The gyro output is used to determine the offsetting rotational requirement that is applied to multiplexer 120 and thence to A/D 122 and microprocessor 124. Microprocessor 124 causes journaling of image sensor 30 in the same manner as described herein above until the gyro outputs an equal and opposite signal indicating that image sensor 30 has journaled back to its original position.

Microprocessor 124 operates on the signal provided from image sensor 30 and thus in effect can be considered to apply a signal to a video driver 136 that in turn provides a signal to drive a video display 52. In practice, the microprocessor does not directly apply a signal to the video driver 136. This display will ordinarily be placed on a shelf or be held by a bracket on a wall or a ceiling. Video display 52 has an upright axis 34 and a lateral axis 36. These axes will generally be viewed as vertical and horizontal. If the image sensor 30 is maintained upright, then the display axes will coincide with the image sensor axes. It will now be seen that rotating the image sensor to maintain its axes in a nominally horizontal and vertical alignment will provide the same orientation to the image on the screen whatever the rotational position of the endoscope may be. As a consequence, the surgeon will remain in a fixed spatial orientation relative to the operating site. He need not exert efforts to orient himself relative to an image that rotates on the display.

As a further advantage, this arrangement displays the full area of the field available from the image sensor. The aspect ratio of the screen 138 and of the image sensor is the same. If the image were rotated, corners and some of the edges of the screen would be blank. Possibly important information from the corners of the image sensor could be lost. This invention does not suffer this risk.

In yet another embodiment of this aspect of present invention, the surgeon may apply a rotational offset to the display image. In this case the surgeon has a preferred viewing angle of the surgical site. The rotational offset is an external value stored by the microprocessor that compensates for angular rotation of the image sensor back to the surgeon's preferred viewing angle. In still another embodiment, both accelerometers and gyros may be employed.

Figure 20:
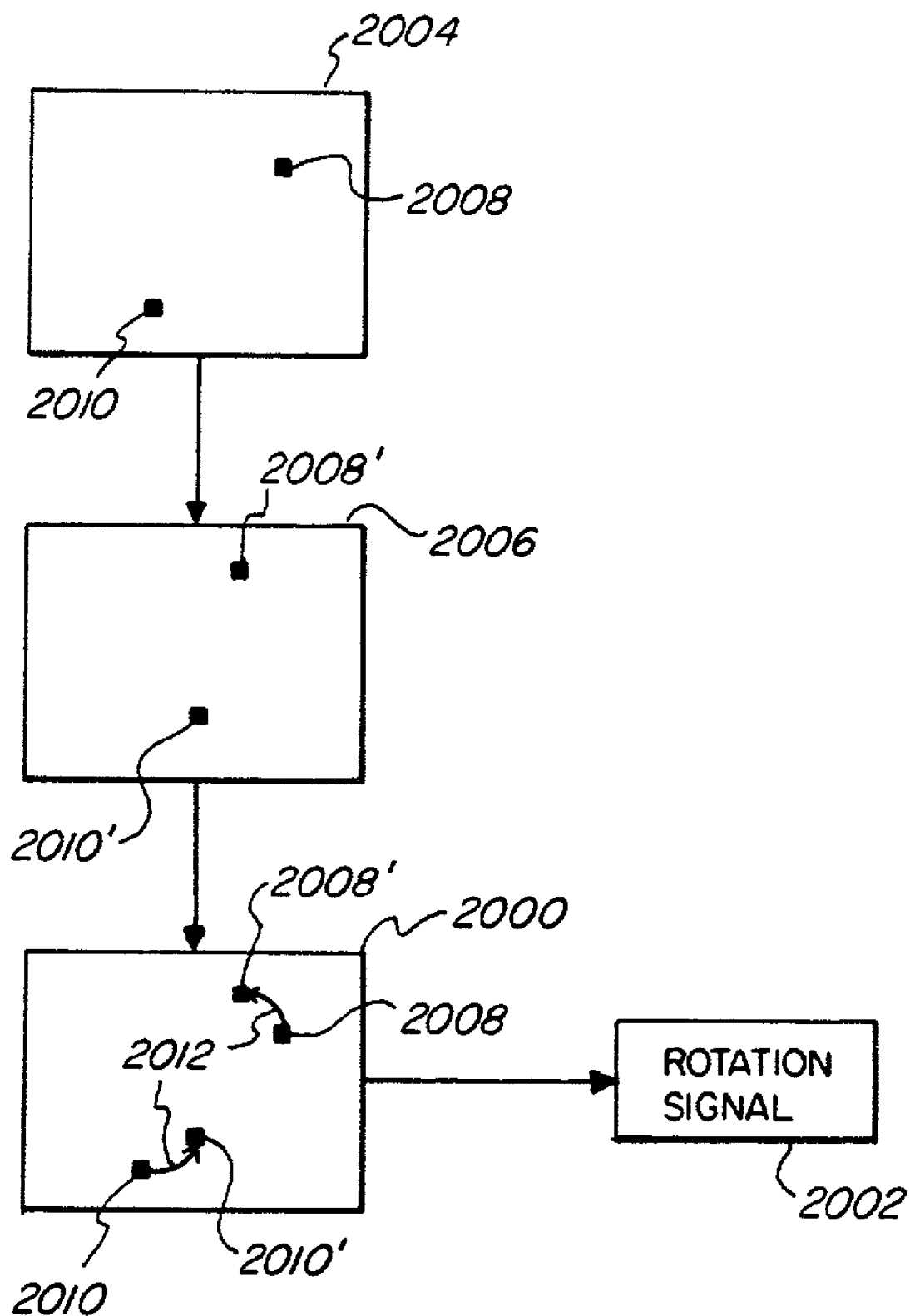
FIG. 20 is a schematic representation of a further embodiment of the present invention in which an image analysis unit is employed to compute a rotation signal.

FIG. 20 illustrates yet a further embodiment of the present invention in which an image analysis unit 2000 is used to compute a rotation signal 2002 for being applied to the image rotator for rotating the image. Image analysis unit compares the signals representative of a first image 2004 with the signals representative of a second image 2006 to determine whether any image rotation has occurred, and then uses this information to generate a compensating rotation signal 2002. In order to accomplish this, one or more reference points 2008, 2010 are located in first image 2004. Such reference points may comprise, for example, bright spots, dark spots, spots having a particular color, shapes, etc. The reference points 2008', 2010' are then located in second image 2006, and image analysis unit 2000 determines whether any rotation has taken place (indicated by arrows 2012). If such rotation has taken place, image analysis unit 2000 computes an appropriate rotation signal 2002 to compensate therefore.

Figure 21:
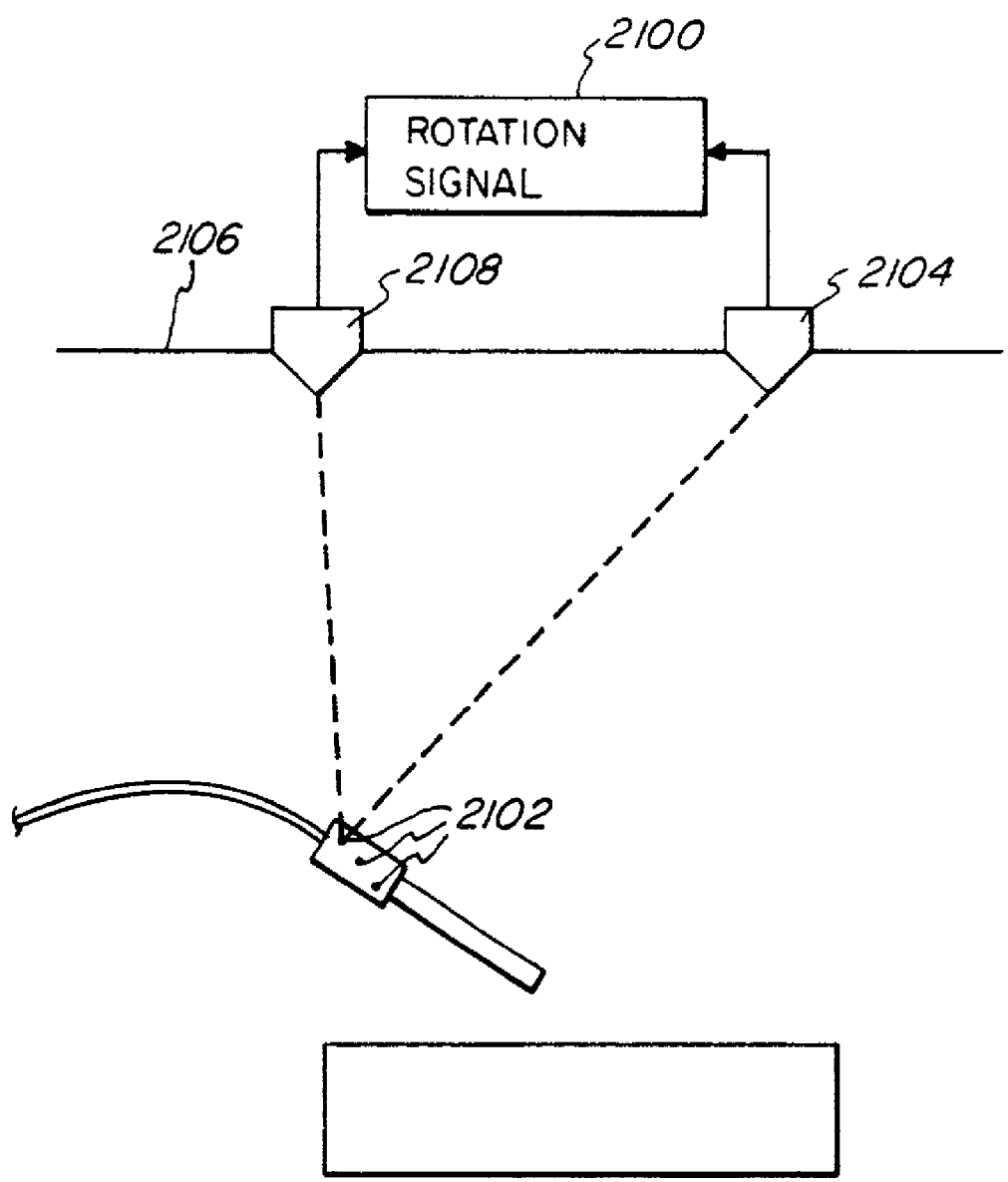
FIG. 21 is a schematic representation a further embodiment of the present invention in which a machine vision system is used to compute a rotation signal.

FIG. 21 illustrates yet a further embodiment of the present invention in which a machine vision system is used to compute a rotation signal 2100 for being applied to the image rotator for rotating the image. In such a system, the endoscope has thereon or therein at least one signal emitting element 2102 which emits some form of energy which is received by a receiver 2104 located at some location remote from the endoscope, such is in the ceiling 2106 of the operating room, mounted on a tripod or the like, or in a wall. By analyzing the energy received from signal emitting elements 2102, receiver 2104 determines the rotation of the endoscope and generates rotation signal 2100 to compensate therefor. Signal emitting elements 2102 may themselves generate the energy, such as in the case of light emitting diodes, magnets, or the like, or may comprise reflectors for reflecting energy emitted from some transmitting source 2108 located at some location remote from the endoscope, such as in the ceiling 2106 of the operating room, mounted on a tripod or the like, or in a wall. Transmitting source 2108 thus transmits energy, which is reflected off signal emitting elements 2102, and is received by receiver 2104. The energy may comprise, for example, infrared energy, light in the visual spectrum, magnetic energy, or the like. For example, if magnetic energy is used, transmitting source 2108 may comprise a remotely located magnetic field generator which "excites" orthogonally positioned coils (i.e., signal emitting elements 2102) within or on a camera head. Dependent upon location of the coils within the magnetic field, the location/orientation of the camera head can be determined by the receiver 2104.

Figure 4:
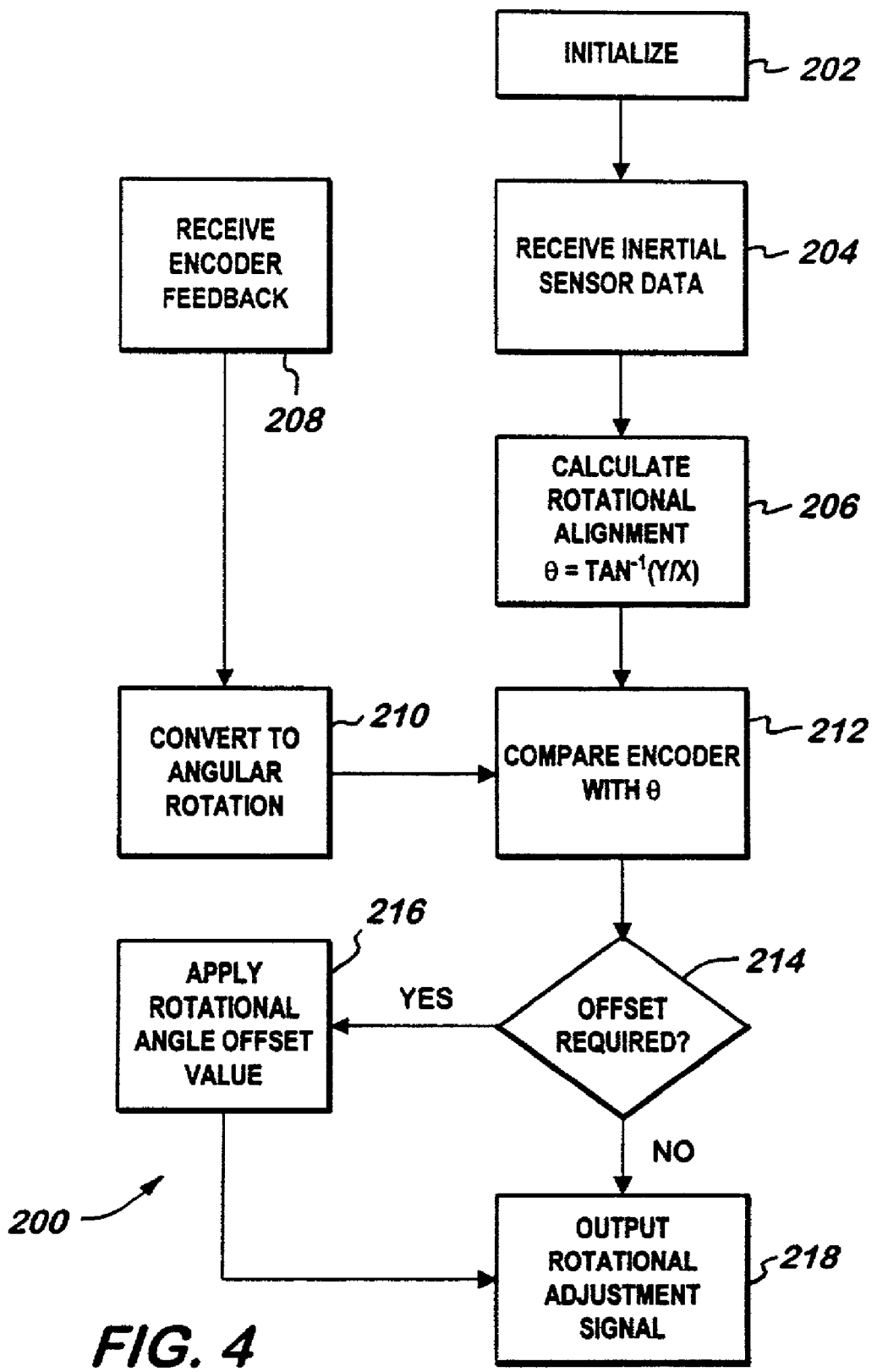
FIG. 4 is a functional flowchart of the control of the of the first embodiment of the invention.

FIG. 4 illustrates a flowchart 200 of the data calculations of the embodiment of FIG. 3. Initialization of circuit elements is accomplished at step 202. In particular, signals are provided and received to assure that any gyros have reached equilibrium and the gyro axis is aligned with either the image sensor lateral or upright axis as necessary. In operation, inertial sensor signals are received at step 204. Based upon these signals, a microprocessor calculates the rotational angle Θ of the image sensor at step 206. Received at step 208 is the output of the encoder. This output is converted into an equivalent encoder rotational angle at step 210 and compared with the image sensor rotational angle at step 212. Based upon this comparison the microprocessor determines if further image sensor rotation is required. In step 214 the system determines whether a particular offset relative to the angle Θ is required by the surgeon. If so, then this is introduced at 216 by varying the angle Θ. The microprocessor then outputs a signal for rotational adjustment of the image sensor axis to cause a desired alignment of the display.

Referring to FIG. 5, an alternative embodiment 300 is illustrated wherein the optical image is rotated before reaching the image sensor 304. In this embodiment, the optical image is rotated rather than the image sensor, to accommodate angular rotation of the endoscope about its optical axis. In an illustrative example of this invention, a prism 302 is interposed between the return of the image from the endoscope's distal end 338 and an image sensor 304 at the proximal end. Prism 302 is of a design that rotation of the prism causes a rotation of an output image for a fixed input image and is described in further detail herein below.

A lens 306 for focusing of the optical image on image sensor 304 may be interposed between prism 302 and image sensor 304. Prism 302 is fixedly disposed on a rotating member 308 whereby a rotation of rotating member 308 rotates prism 302 an equivalent angular amount. For simplicity, prism 302, object lens 306, and image sensor 304 are all shown aligned along the same axis. Other lens and prism arrangements may be used to direct the optical image as necessary. A microprocessor 310 receives an angular rotation signal on a line 340 from an inertial sensor (not shown) attached to prism 302 (or prism rotating member 308) that is proportional to the angular displacement of the optical axis of prism 302. Microprocessor 310 outputs an rotational adjustment signal to an amplifier 312 which amplifies the signal to provide an electrical drive for a motor 314. A first driver 316 is affixed to the motor output shaft 315 and is operably connected to a second driver 318 which is in turn operably connected to rotating member 308. Hence motor 314 output rotation is transferred via drivers 316 and 318 to cause journaling of rotating member 308 and prism 302 affixed thereon.

Second driver 318 is mounted on an encoder shaft 320 of an encoder 322 whereby rotation of second driver 318 causes rotation of encoder shaft 320. Encoder 322 provides an image rotation signal on a line 324 that is proportional to shaft 320 rotation. Image rotation signal 324 provides feedback to microprocessor 310 for determining when prism 302 has rotated a sufficient amount to counterbalance the output from the inertial sensor (not shown).

A Pechan prism, well known to those of ordinary skill in the art, is an example of a prism having the rotational characteristics desired and is illustrated in top view as 326 in FIG. 6A and front view 327 in FIG. 6B. The prism has an optical axis 328. Surfaces 334 and 336 are silvered. An input image 330 to Pechan prism 326 results in an output image 332 that is rotated through an angle of $\pi$ radians (180°) about optical axis 328 and that is also rotated through an angle of $\pi$ radians (180°) about an axis perpendicular to optical axis 328. It is a feature of the Pechan prism that rotation of the prism about its optical axis causes the output image to rotate at twice the angular velocity with respect to the rotation of the prism.

Other optical image inversion prisms than a Pechan prism can be used such as a Dove prism, reversion prism, Taylor prism and other compact prisms. It should be understood that while a received image from an inversion prism may have been re-oriented, it also often results in a mirror image of the original image. This mirror image will have to be corrected either by an optical element such as another prism, or preferably by using electronic means. When a camera head uses such inversion prism, the microprocessor, such as 310 in FIG. 5, is provided with software steps which automatically "reverse" the image prior to display. This can be done as part of the video processing as well. Techniques to electronically reverse an image are well known and need not be further described.

Figure 7:
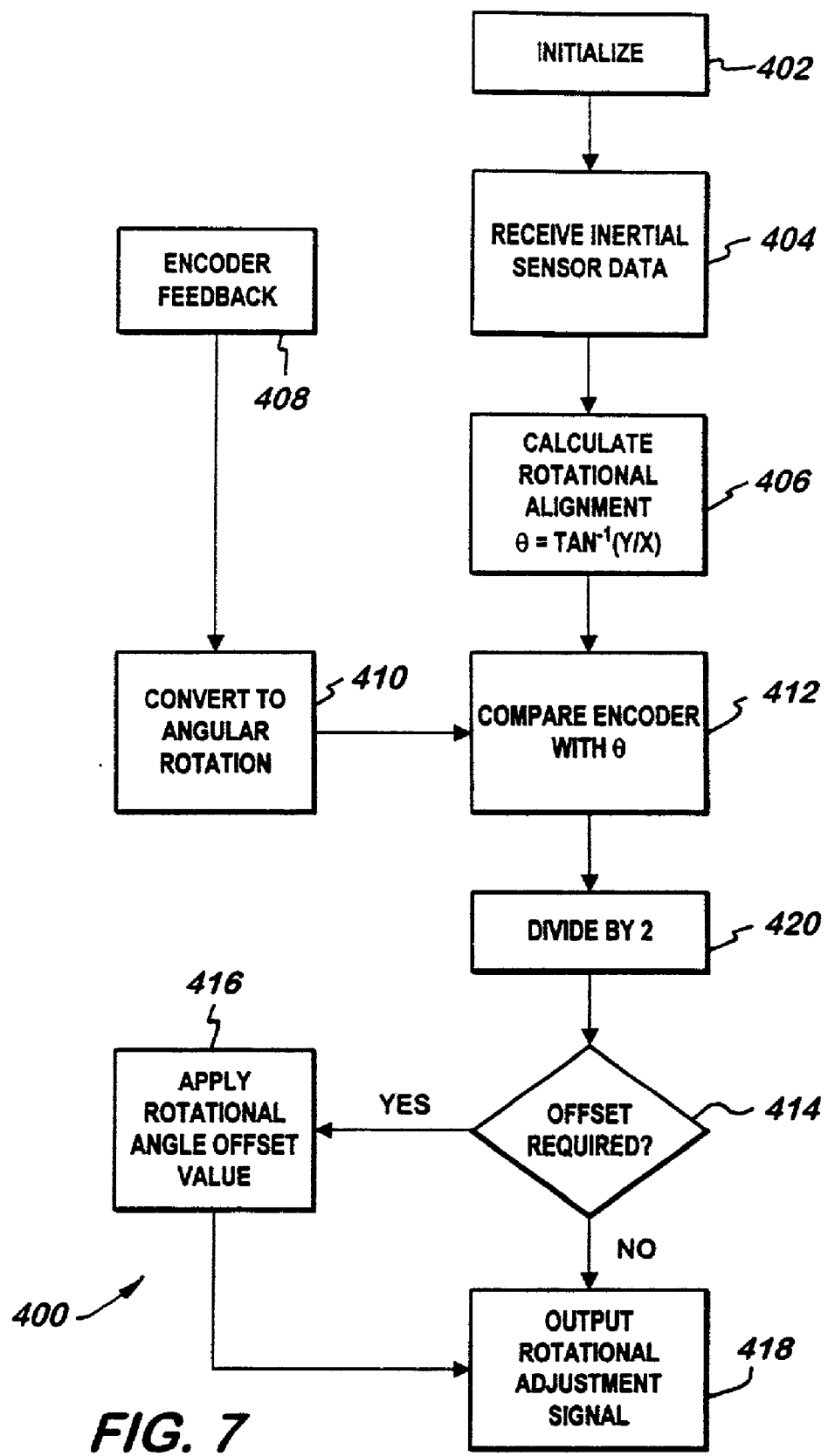
FIG. 7 is a flowchart of the control steps of the of an alternative embodiment of the invention.

FIG. 7 illustrates a flowchart 400 of the data calculations of the embodiment of FIG. 5. Initialization of circuit elements is accomplished at step 402. In particular, signals are provided and received to assure that any gyros have reached equilibrium and the gyro axis is aligned with either the image sensor lateral or upright axis as necessary. In operation, inertial sensor signals are received at step 404. Based upon these signals, a microprocessor calculates the rotational angle θ of the image sensor at step 406. Received at step 408 is the output of the encoder. This output is converted into an equivalent encoder rotational angle at step 410 and compared with the image sensor rotational angle at step 412. Based upon this comparison the microprocessor determines if further image sensor angular rotation is required. The calculated image sensor angular rotation is divided by two (2) in step 420. This division is necessary because it is a feature of the Pechan prism that rotation of the prism about its optical axis causes the output image to rotate at twice the angular velocity with respect to the rotation of the prism. In step 414 the system determines whether a particular offset relative to the angle Θ is required by the surgeon. If so then this is introduced at 416 by varying the angle Θ. The microprocessor then outputs a signal for rotational adjustment at step 418 of the image sensor axis to cause a desired alignment of the video display.

Figure 8:
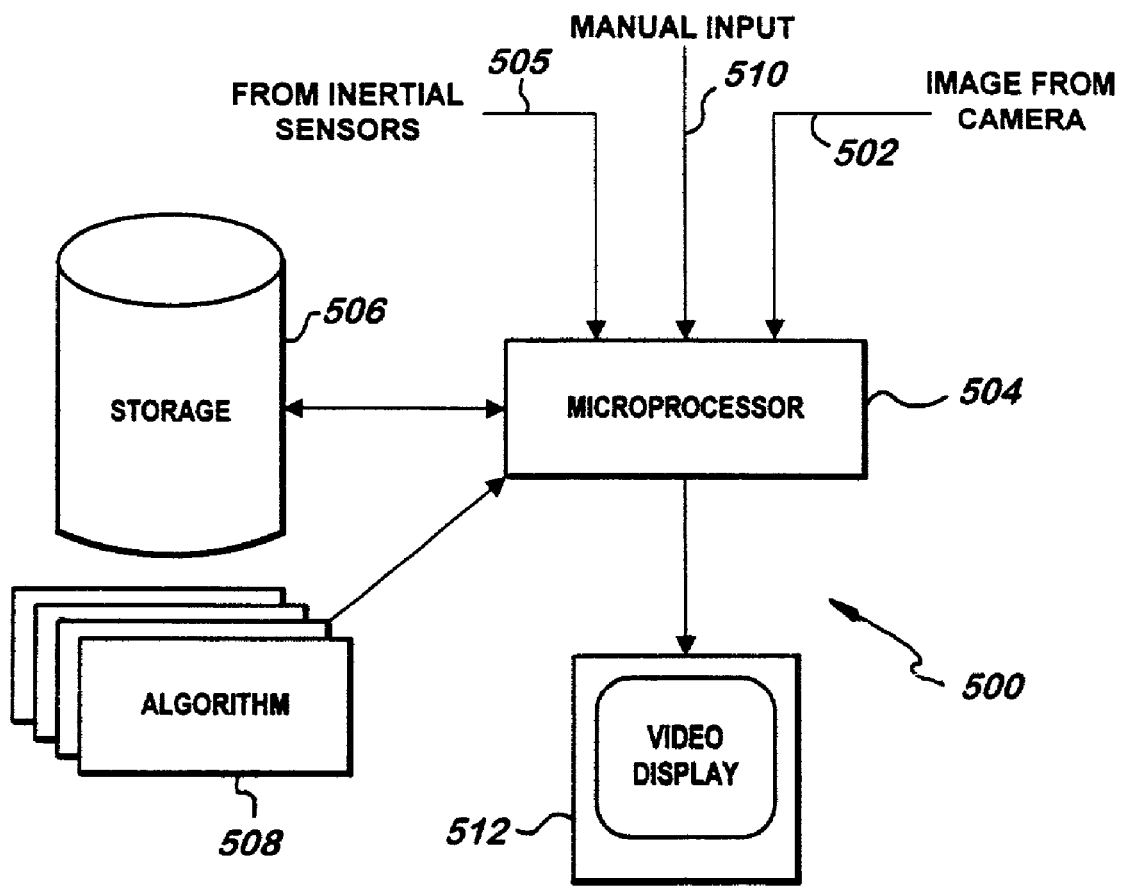
FIG. 8 is a diagrammatic representation of an electronic correction for a rotation of an image sensor about its optical axis.

In yet another embodiment, the change in rotational alignment of the display can be done electronically within a microprocessor as shown diagrammatically as 500 in FIG. 8. The image sensor image 502 is received by a microprocessor 504, digitized and stored in a storage medium 506. Microprocessor 504 receives the relative angular rotation requirement, Θ, from the inertial sensors on a line 505. Microprocessor 504 retrieves the digitized image from storage medium 506 and adjusts each part of the image for the rotation requirement in accordance with an appropriate affine algorithm 508. An external rotational offset 510 may also be input to microprocessor 504 to establish a vertical image offset view preferred by the surgeon. This manual input is used as an offset in algorithm 508. The result of the algorithm is used to drive the video display 512 to present a display image orientation corrected for the relative angular rotation requirement.

In yet another exemplary embodiment of the present invention, corrections may be made for image distortions due to perspective variations. These perspective variations result from the obliqueness of the endoscope's distal end with respect to an image. The obliqueness of an image is determined by ascertaining an angular orientation of the image sensor in both the x-z and y-z planes as distinguished from the rotational adjustment for angular variations about the optical axis as previously discussed.

Figure 9A:
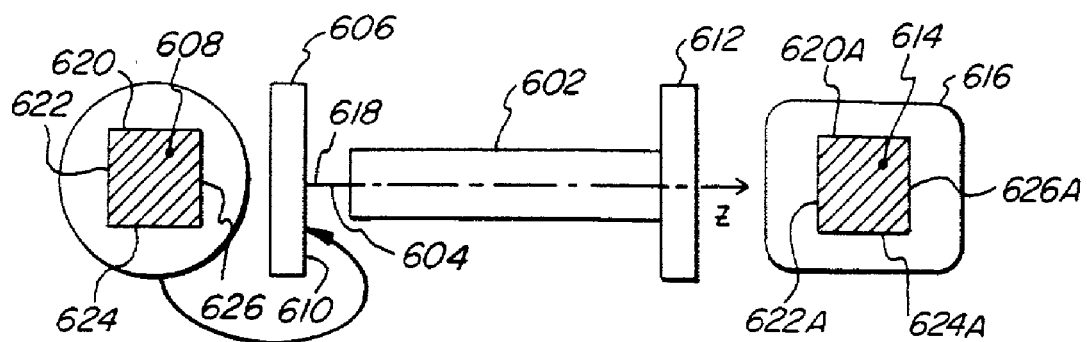
FIGS. 9A–9C are diagrams of the distortion of an image on a video display as a result of the oblique orientation of an image receiving device to an image.
Figure 9B:
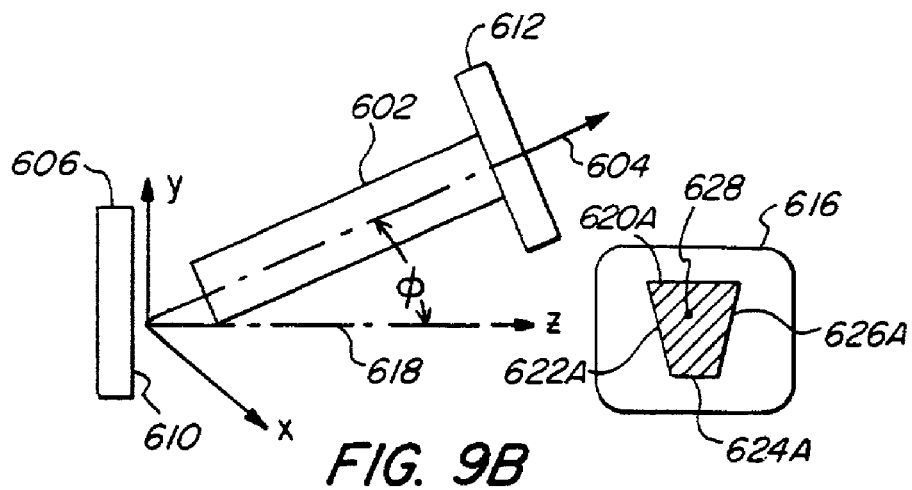
Figure 9C:
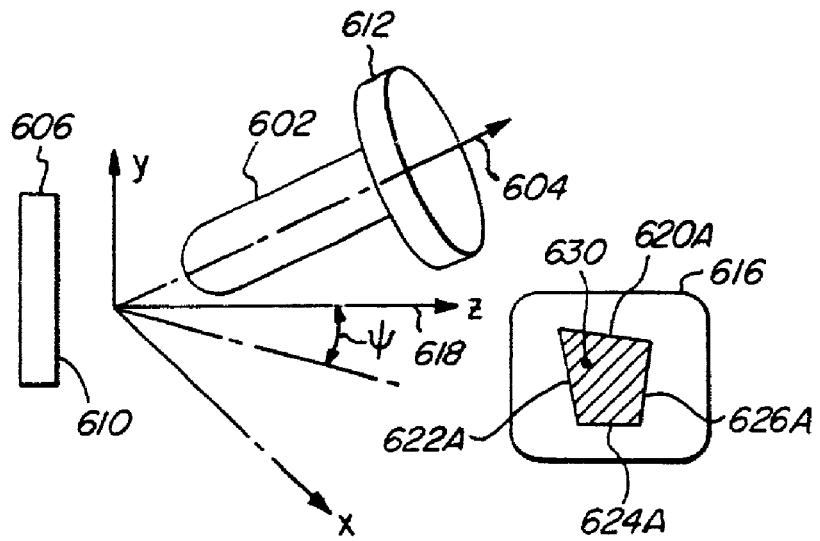

FIG. 9A–C illustrate the difficulty associated with the "obliqueness" of a view causing a "perspective distortion" on the visual display. Referring to FIG. 9A, an endoscope image forwarding system 602 is shown wherein an optical axis 604 of forwarding system 602 is coincident with a horizontal z-axis 618 and is perpendicular to an image surface 606. An image of a square 608 is an illustrative actual view 610 of endoscope 602 to illustrate the perspective distortion. Square 608 has sides 620, 622, 624, and 626. An image sensor 612 receives actual view 610 and a resultant image 614 is shown on a video display 616. Resultant image 614 accurately reflects actual view 610 because of the perpendicular relationship between optical axis 604 and image surface 606. Resultant image 614 has sides 620A, 622A, 624A, and 626A corresponding to sides 620, 622, 624, and 626 of square 608, respectively.

In FIG. 9B optical axis 604 of endoscope 602 is raised by an angle, Φ, above horizontal axis 618. Image sensor 612 receives a perspective view of actual square image 610. That is, actual image 610 will appear to have a first vanishing point below image surface 606. Lines that do not converge at the vanishing point, such as line 620, which are closer to the end of the endoscope 602 will appear longer than those further away such as line 624. Lines converging at the vanishing point, such as lines 622 and 626, will appear foreshortened. Image sensor 612 will receive this view and a resultant display 628 is shown on video display 616. Square 608 appears as a trapezoidal shape 628 on video display 616. Side 620A appears longer than side 624A and sides 622A and 626A appear foreshortened.

In FIG. 9C, in addition to being raised above horizontal axis 618, optical axis 604 of endoscope 602 is angled away from the y,z plane, by an angle ψ. The y,z plane is the plane of the drawing. Actual image 610 will appear to have a first vanishing point below and a second vanishing point to the right (or into the plane of the paper) of image surface 606. Lines that converge to the first vanishing point below actual image 606, such as lines 622 and 626, will appear foreshortened. Lines which are closer to the end of the endoscope 602, such as line 620 will appear longer than those further away such as line 624. Lines converging at the second vanishing point, such as lines 620 and 624, will appear foreshortened. Lines which are closer to the end of the endoscope 602, such as line 622 will appear longer than those further away such as line 626. Image sensor 612 will receive this view and a resultant display 630 is shown on video display 616. Square 608 appears as an irregular quadrilateral. The result for the surgeon is a warped view wherein side 622A appears higher and longer than side 626A and the two lines are not parallel; side 620A appears longer than 624A and these two lines also appear to be not parallel. This may be disconcerting to a surgeon who expects the anatomy to appear in very specific spatial relationships.

The use of gravity sensing accelerometers will produce the angular corrections necessary. However, just as in the aforementioned optical axis rotation of the x-y plane, two accelerometers in each plane advantageously enables one to define automatic adjustment of the display for a variety of rotations about various axes for the output signals from both accelerometers.

Image modification for obliqueness is done by application of an affine algorithm to a digitally stored image. In addition to the correction for the angular rotation about the x- and y-axes, the algorithm may also include factors to warp or perspective-distort the image, if desired, then display the transformed image on a video display.

Figure 10:
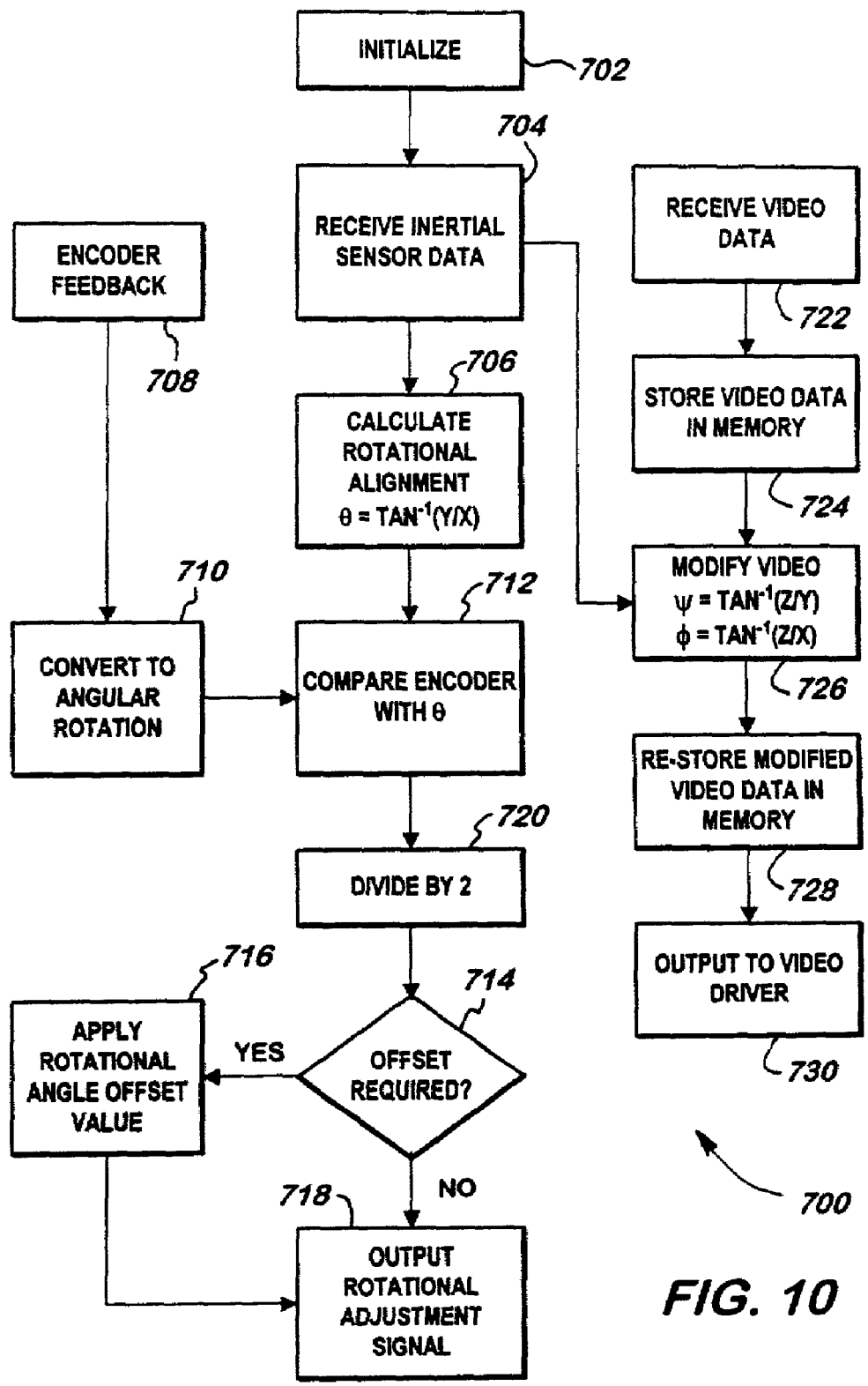
FIG. 10 is a flowchart of the control steps of a third embodiment of the invention wherein both image sensor rotation and perspective distortions are corrected.

FIG. 10 illustrates a flowchart 700 of the data calculations for the perspective distortion caused by an oblique endoscope view of an image as described herein above in FIG. 9. Initialization of circuit elements is accomplished at step 702. In particular, signals are provided and received to assure that any gyros have reached equilibrium and the gyro axis is aligned with either the image sensor lateral, upright, or optical axis as necessary. In operation, inertial sensor signals are received at step 704. Based upon these signals, a microprocessor calculates the rotational angle θ of the image sensor at step 706. Received at step 708 is the output of the encoder. This output is converted into an equivalent encoder rotational angle at step 710 and compared at step 712 with image sensor rotational angle calculated at step 706. Based upon this comparison the microprocessor determines if further image sensor angular rotation is required. The calculated image sensor angular rotation is divided by two (2) in step 720 if a Pechan prism is used as described herein above. In step 714 the system determines whether a particular offset relative to the angle Θ is required by the surgeon. If so then this is introduced at 716 by varying the angle Θ. The microprocessor then outputs a signal for rotational adjustment at step 718 of the image sensor axis to cause a desired alignment of the display.

Video data is received from the image sensor at step 722. Video data 722 is digitized and stored in computer memory at step 724. Inertial data received at step 704 is used to calculate obliqueness angles psi, Φ, and phi, ψ, at step 726. Digitized video image 724 is retrieved from memory and modified using angles Φ and ψ in step 726. Modified video image 726 may be stored again in memory at step 728. Modified video image 726, corrected for perspective distortion is output to a video driver at step 730. The video driver is a device adapted to receive digitized video signals and provide a drive signal for presentation of an image on a video display. Hence, the perspective distortion of an image received from an image sensor is corrected through the application of a mathematical algorithm applied to the received image. Correction for rotation about the optical axis of the image sensor may be accomplished either through a mechanical manipulation of the received video image as described herein above. Alternatively, correction for rotation about the optical axis may also be accomplished through application of a mathematical algorithm to the received video signal from the image sensor.

Figure 11:
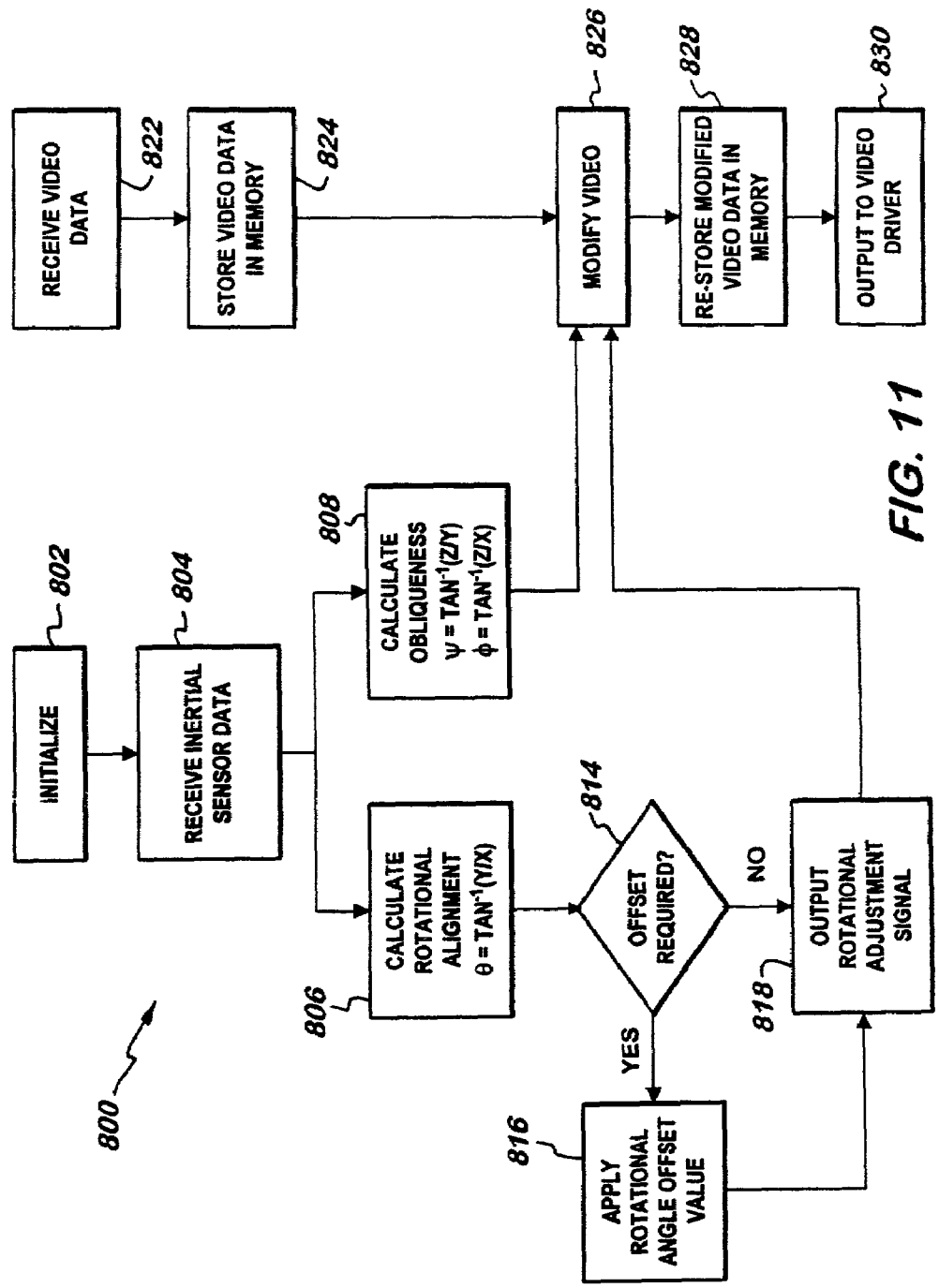
FIG. 11 is a functional flowchart of the control of a fourth embodiment of the invention wherein both image sensor rotation and perspective distortions are corrected by electronic means.

FIG. 11 illustrates a flowchart 800 wherein the data calculations for the rotation of the image sensor about its optical axis as well as the perspective distortion caused by an oblique endoscope view of an image is accomplished by application of mathematical algorithms to the received video signals. Initialization of circuit elements is accomplished at step 802. In particular, signals are provided and received to assure that any gyros have reached equilibrium and the gyro axis is aligned with either the image sensor lateral, upright, or optical axis as necessary. In operation, inertial sensor signals are received at step 804. Based upon these signals, a microprocessor calculates the rotational angle θ of the image sensor at step 806 and perspective distortion angles Φ and ψ at step 808. In step 814 the system determines whether a particular offset relative to the angle θ is required by the surgeon. If so then this is introduced at 816 by varying the angle θ. The microprocessor then outputs a signal for rotational adjustment at step 818 of the image sensor axis to cause a desired alignment of the display.

Video data is received from the image sensor at step 822. Video data 822 is digitized and stored in computer memory at step 824. Digitized video image 824 is retrieved from memory and in step 826 is modified using perspective distortion angles φ and ψ calculated in step 808 and rotational adjustment angle theta, θ, calculated in step 818. Modified video image 826 may be stored again in memory at step 828. Modified video image 826, corrected for perspective distortion and angular rotation is output to a video driver at step 830. The video driver is a device adapted to receive digitized video signals and provide a drive signal for presentation of an image on a video display. Hence, both the perspective distortion and angular rotation of an image received from an image sensor is corrected through the application of a mathematical algorithm applied to the received image.

Figure 12:
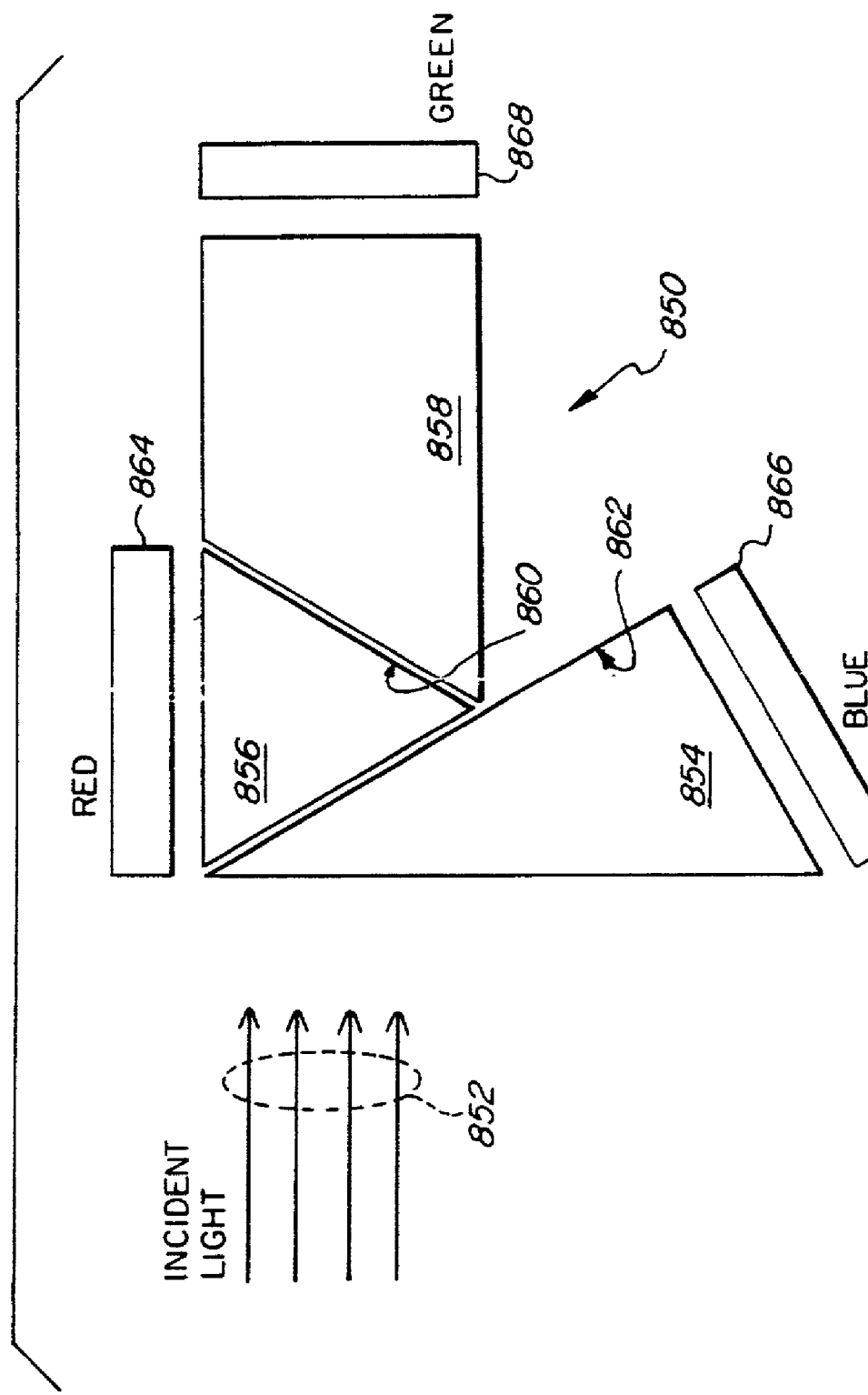
FIG. 12 is a diagram of prisms used to separate incident light into three components of light.

FIG. 12 illustrates an apparatus employing prisms 850 for color separation. Incident light 852 is directed perpendicularly to the surface of a three-part prism comprised of prisms 854, 856, and 858. Surface 860 of prism 856 has a red coating whereby the red component of the incident light is reflected to the red image sensor 864. In a similar manner, surface 862 of prism 854 has a blue coating whereby the blue component of the incident light is reflected to the blue image sensor 866. The remaining component of the light is allowed to pass through the prism 858 to the green image sensor 868. In this manner the incident light is divided into three components.

Figure 13:
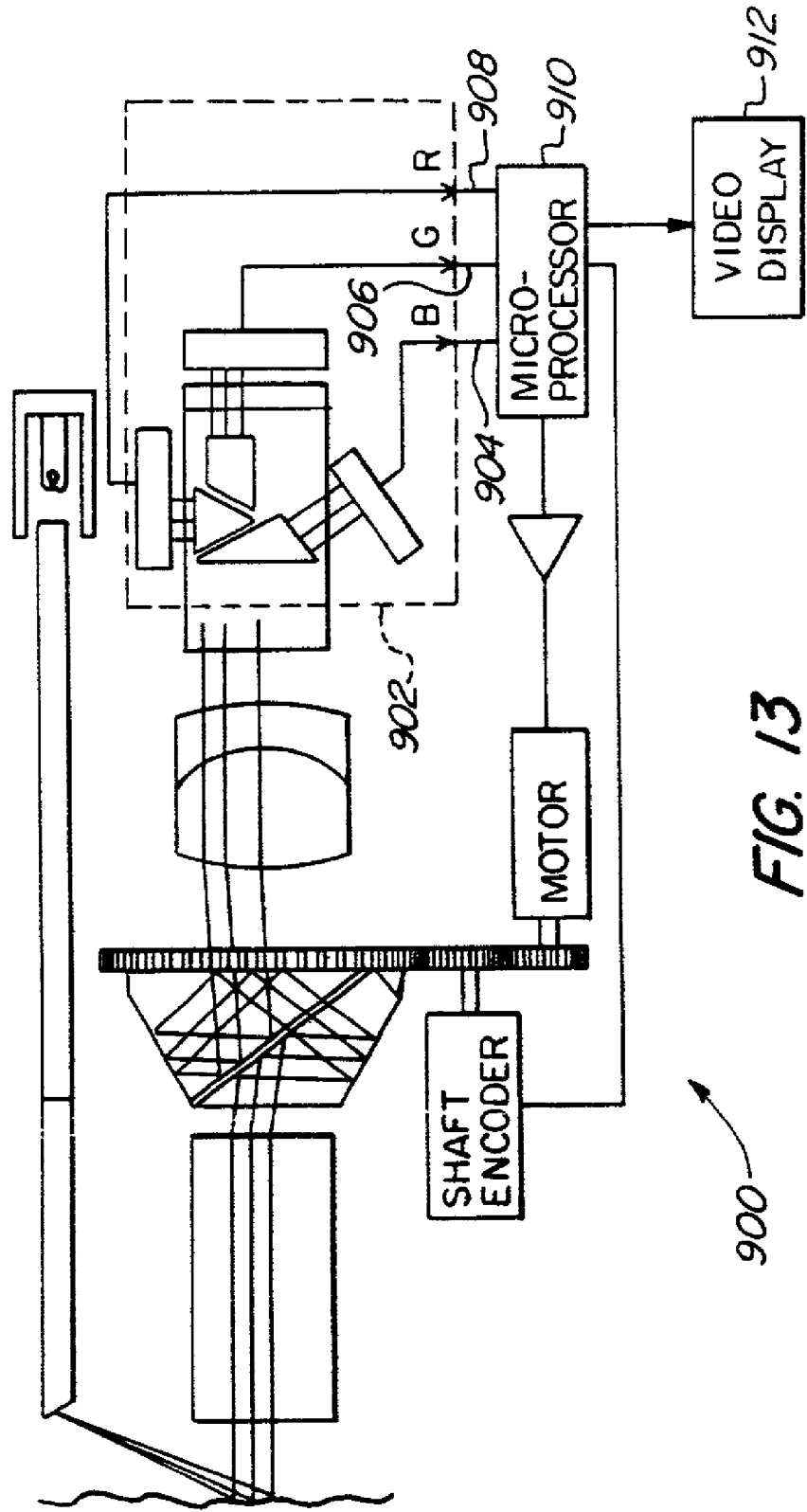
FIG. 13 is a schematic diagram illustrating an apparatus and control system of a fifth embodiment of the invention resulting in a color display.

Referring to FIG. 13, the color separator of FIG. 12 is shown as 902 in the color image sensor system 900. Color separator 902 generates a image sensor signal for each of the color components blue 904, green 906, and red 908. Signals 904, 906, and 908 are received by a microprocessor 910, combined and displayed on a video display 912 as shall described in more detail herein below. The rotational modification is otherwise performed in a manner equivalent to that described in the monochromatic system of FIG. 5.

FIG. 14 diagrammatically illustrates a color system 950. The image sensor images 952, 954, and 956 are received by a microprocessor 958, digitized and stored in a storage medium 960. Microprocessor 958 also receives the relative angular rotation requirement, θ, from the inertial sensors on line 962. Microprocessor 958 retrieves the digitized images from storage medium 960 and combines each picture element in accordance with an appropriate algorithm 964. Rotation of a prism to account for the rotational deviation has been described herein above. An affine algorithm may alternatively be applied in lieu of the prismatic rotational embodiment. A manual input 966 may also be input to microprocessor 958 to establish a vertical image offset view preferred by the surgeon. This manual input is used as an offset in affine algorithm 964. The result of the algorithms is used to drive a color video display 968 to present a color display image orientation corrected for the relative angular rotation requirement.

FIGS. 15A–15G illustrate an embodiment in which at least one rate gyro 1500 and at least one accelerometer 1505 are mounted to an image sensor 1510 so that both inertial sensors rotate with the image sensor 1510 within a camera head 1515. The camera head 1515 is attached to a suitable endoscope.

While the camera head 1515 is held horizontally with respect to the ground, as suggested by arrow 1535, and as shown in FIGS. 15A, 15B and 15C, accelerometer 1505 outputs a signal level that corresponds to the direction of gravity as represented by arrow 1520. The accelerometer output signal is used to control the rotation of the image sensor 1510 and its attached assembly containing gyro 1500 and accelerometer 1505. Control over the rotation can in this mode be done as described in the U.S. Pat. No. 6,097,423. As described in this patent, as the camera head 1515 is rotated as suggested by arrow 1525 in FIG. 15C and the marker 1540, the image sensor 1510 is rotated to re-orient the resulting displayed video image.

Figure 16:
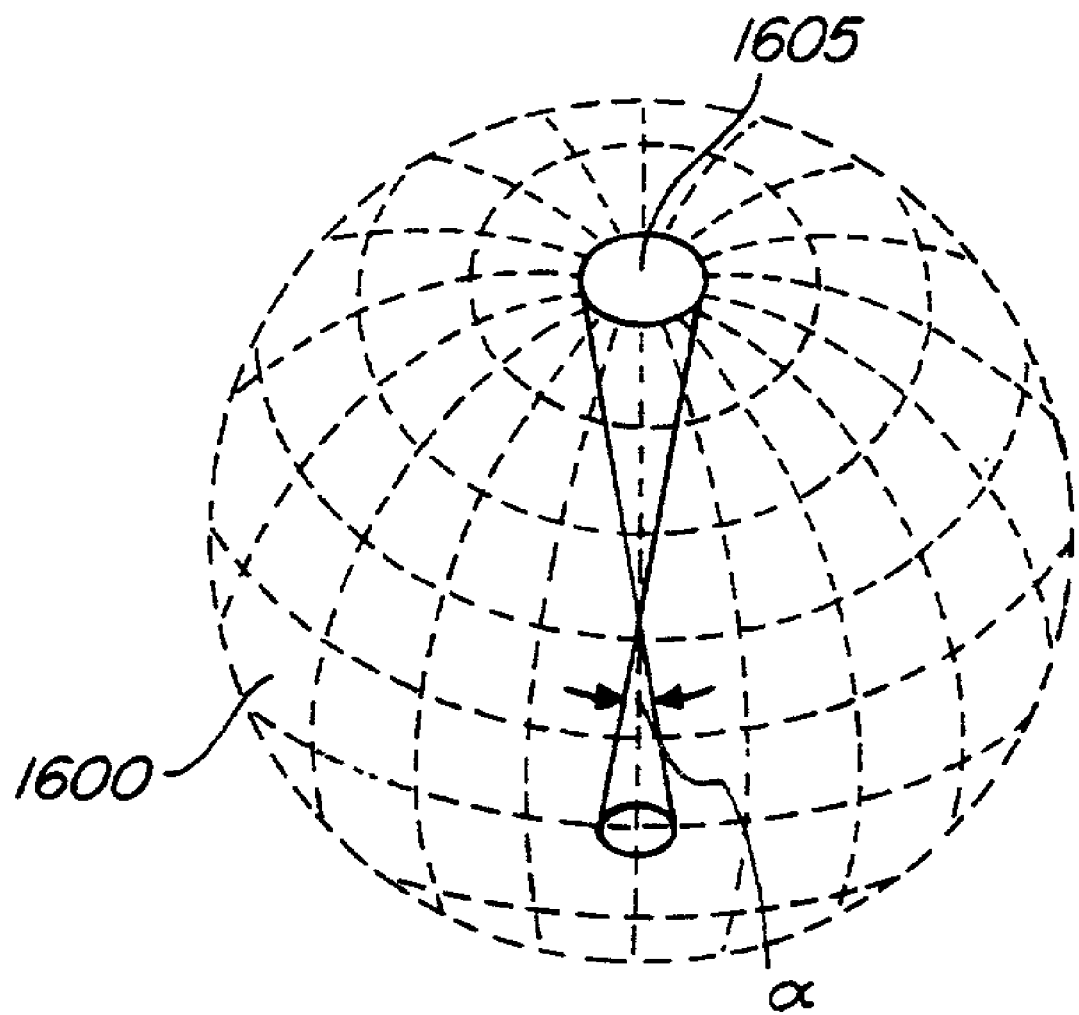
FIG. 16 is a schematic representation of control regimes for image rotation using gyro and accelerometer inertial sensors.

When the operative direction 1530 of camera head 1515, namely its elevation angle, is positioned closer to the vertical, represented by the arrow 1520 and the Y axis in FIG. 15D, the position becomes closer to the direction of gravity. This can occur either with the camera head pointing up or down. The accelerometer output signal then becomes less reliable for use in re-orienting the displayed image due to a subsequent rotation by the operator of the instrument 1515. This arises because the accelerometer is limited to providing a valid rotational control signal or voltage only within the zone identified in FIG. 16 at 1600 as the accelerometer control zone. By "valid" it is meant that the accelerometer can detect gravity and output a signal that is adequate for rotation control.

But, as the camera head 1515 or its operative direction 1530 approaches perpendicularity, i.e. parallel to the Y axis and the force of gravity, a spatial angle will be reached where the accelerometer can no longer output a valid signal adequate for rotational control. Beyond this angle, the gyroscope 1500's output signal is employed to detect rotation of the camera head 1515 relative to or about the axis 1535 of the instrument. The gyro's output signal is then used to control the rotation of the image sensor 1510, accelerometer 1505 and gyro 1510 assembly. The angular region or zone where the gyro output signal is used for rotational control is identified at 1605 in FIG. 16. This angular region has a conical shape and is defined by the solid angle α.

A common, undesired characteristic of gyroscopic devices is called drift. This drift results in an output signal from the gyro indicating a rotational change, even if no actual corresponding rotation has occurred. Additionally, drift will affect the accuracy of the gyro's output signal when a rotation change does occur. Typically, the longer a gyroscope is energized, the greater the accumulated angular drift. Hence, in accordance with one aspect of the invention, the gyro output is not used while the camera head 1515 angular tilt from horizontal, i.e. its elevation, is within the accelerometer zone 1600. In such case the gyro drift does not matter. However, when the camera head position crosses into the gyro zone 1605, control is transferred to the gyro output and at the same time a correction of the gyro output is made.

The correction of the gyro output can be made so as to in effect zero out its output signal. Alternatively, since the angular position of the gyro zone 1605 is known, namely 90° less half of α, the gyro output signal indicative of the gyro elevation can be made equal to a value that is indicative of that angle when the instrument's operative or tilted axis 1635 reaches an angle equal to that. Hence, while the instrument's operative axis 1635 bears an angle greater than 90° less half of α, the gyro output controls image rotation.

Though the gyro continues to introduce drift while the instrument head is within the gyro zone 1605, the drift error still tends to be minimized. This arises because every time that the instrument enters the accelerometer zone 1600 and then reenters the gyro zone 1605 the gyro output is corrected for drift.

Figures 17, 18:
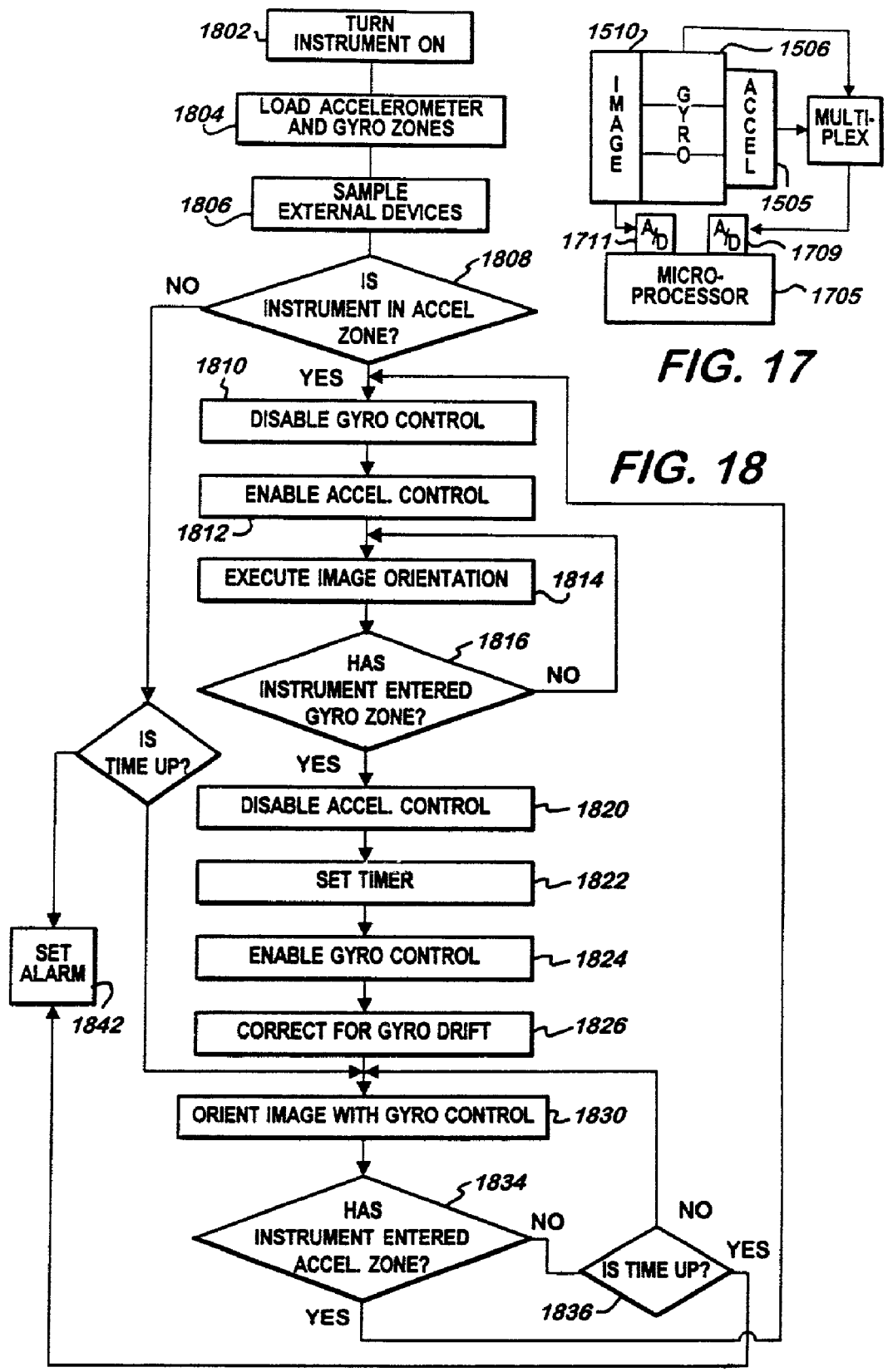
FIG. 17 is a block diagram view of one control using gyro and accelerometer inertial sensors in accordance with the invention.
FIG. 18 is a flow chart illustrative for implementing a gyro and accelerometer control over the re-orientation of an image obtained through an endoscope.
Figure 19:
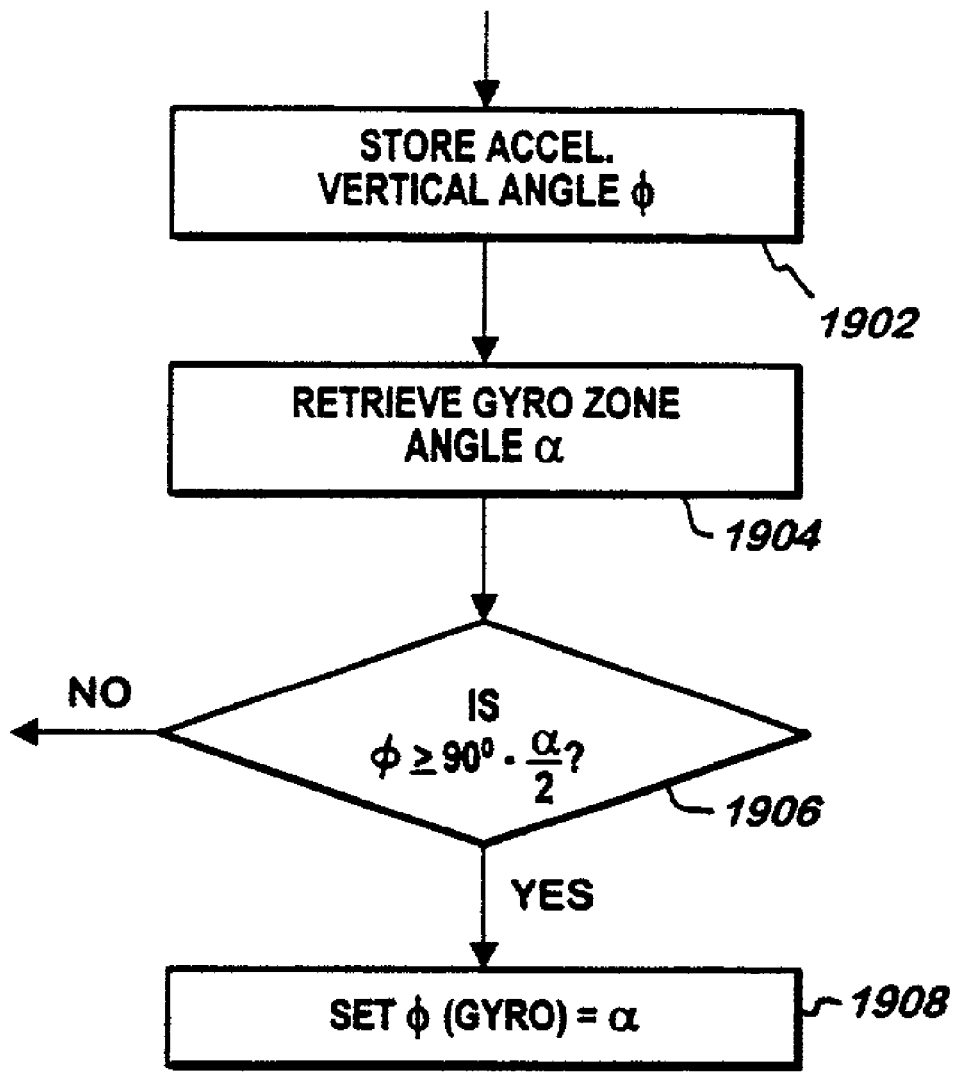
FIG. 19 is a flow chart illustrative for implementing certain aspects o the flow chart in FIG. 18.

FIGS. 17 through 19 illustrate one technique for handling image rotation using both an accelerometer 1505 and a gyro 1500. These devices are mounted to an image sensor, such as a CCD and cause it to rotate for correction of a displayed image. FIG. 17 illustrates, like in FIG. 15A, these devices coupled to a microprocessor 1705, which can be similar to processor 124. A multiplexer 1707 can be used to alternately sample the outputs respectively from the gyro 1500 and accelerometer 1505 and then, through an A/D converter 1707, enter the digital values into the processor 1705. The output from the CCD image sensor 1510 is also entered through an A/D converter 1711 into the processor 1705 using techniques as are well known in the art.

The processor 1705 is provided with a program with which it can perform the functions needed to properly switch control over image rotation between the gyro 1500 and accelerometer 1505. FIG. 18 illustrates a technique 1800 including steps that can be used to implement this control. Thus at 1802 the instrument is turned on and causes at 1804 the loading into memory of the particular limits applicable to the accelerometer and gyro zones 1600 and 1605. The values defining these zones can be stored in a permanent memory from which they are extracted when needed The external devices, including the gyro and accelerometer outputs and the CCD in the image sensor 1510, are sampled and their values are stored at 1806.

These values include angle Φ as sensed by the accelerometer 1505. At step 1808 a test is made as to whether the instrument as determined by the values Φ obtained by the accelerometer are less than 90°—half of α. If so, the processor makes a determination that the instrument is within the accelerometer zone and disables the gyro control at 1810 and enables the accelerometer control at 1812.

At this point an image rotation control is activated at 1814 such as described with reference to FIG. 4 while using the accelerometer output signal. A test is regularly made at 1816 to determine whether the instrument has entered into or crossed the boundary of the gyro zone 1605. If not, a return is made to continue the accelerometer control at 1814. However, if such crossing is detected, the accelerometer control is disabled at 1820 and a timer 1822 may be set. Such time measurement may be deemed desirable in order to obtain information how long the instrument has been under gyro control, and thus how much drift may have occurred.

The gyro control is then entered at 1824 and the output of the gyro is corrected 1826. This correction can be by setting the elevation value of its output within the processor 1705 such as to zero or to a level indicative of the actual elevation value represented by the solid angle α, namely 90° less half of α. The correction can be applied to other steps within the microprocessor 1705. Image orientation control is then done, within the gyro zone 1605, at 1830 under control by the gyro output signal.

A test is made at 1834 whether the instrument has been moved so as to cause it to leave the gyro zone 1605. If not a return is made to step 1830 after determining at 1836 how long the instrument has been in the gyro zone without having been corrected for drift. This can be done by detecting whether the timer has timed out or by using another time interval measuring technique. If the instrument has left the gyro control zone 1605 then a return is made to step 1810 at the start of an accelerometer control cycle.

Note that if the test at 1808 indicated that the instrument is within the gyro zone, control can either be transferred to step 1830 or by setting an alarm since one is not always sure how long this condition may have existed and too much gyro drift may have occurred for reliable gyro control. Similarly, a test can be made at 1840 whether the timer set at 1822 has timed out to indicate to the user, such as by way of an alarm set at 1842, that the instrument has operated too long under gyro control, or take such other action as appears appropriate.

FIG. 19 illustrates one technique for determining whether the instrument has moved from the accelerometer control zone 1600 to the gyro control zone 1605. Thus at step 1902 the accelerometer vertical angle φ is stored and the value of the angle α is retrieved at 1904. A test is then made at 1906 whether the output angle φ is equal to or greater than 90° less half of α. If so the elevation signal value from the gyro control is set equal to 90° minus α at 1908 and a return to step 1820 is made. If the test at 1906 resulted in a negative answer, control remains with the accelerometer and a return to step 1814 is made.

Having thus described several embodiments in accordance with the invention to correct the rotational display of an image, obtained with a camera affixed to an endoscope, variations can be made by one with skill in the art without departing from the scope of the claims herein.

For example, the accelerometers 40, 42 in FIG. 3 need not be mounted so as to rotate with the image sensor 30. In such case the microprocessor 124 needs to correlate the accelerometer voltage to the image sensor. For instance, if the accelerometer output is zero volts DC, the instrument's head is level and no image rotation is to occur. As the accelerometer output voltage changes, the microprocessor 124 will have to derive the image sensor to be in a particular position corresponding to the voltage offset from the zero or horizontal level.

In many cases it is more practical to mount the inertial sensors and image sensor rigidly to a camera head. In such case the outputs from the inertial sensors is used for an electronic image rotation within the microprocessor.

When a gyro is fixed to the instrument or camera head frame and the accelerometer and image sensor assembly rotate, the technique of FIGS. 15 through 19 still hold. As rotation is detected by the gyro, such as when the head of the instrument is in the gyro control zone 1605 of FIG. 16, the image sensor and accelerometer assembly is inversely rotated to hold the displayed image orientation.

Accordingly, this invention is not to be limited by the embodiments shown in the drawings and described in the description, since these are given by way of example and not of limitation.

What is claimed:

1. A video camera system for modifying an image received by an endoscope, comprising:
    a) an image sensor mounted to the camera system and having a sensor optical axis, said sensor being aligned to receive said image and provide image signals representative of said image;
    b) an image analysis unit which compares image signals representative of a first image with image signals representative of a second image to provide a rotation signal representative of angular rotation of said image sensor;

c) a processor responsive to said image signals and the rotation signal; and d) said processor including an image rotator processor for rotating the image represented by the image signals by an amount effectively determined by said rotation signal and producing display signals indicative of the rotated image.

2. A video camera system for modifying the orientation of a display of an image received by an endoscope, comprising:

a) an image sensor having a sensor optical axis aligned to receive the image to provide image signals representative of said image and having a vertical reference;

b) an image analysis unit which compares image signals representative of a first image with image signals representative of a second image to provide a rotation signal representative of angular orientation of said image sensor around said sensor optical axis; and c) an image rotator responsive to said rotation signal to produce display signals for a display of said image with a rotation in a direction that establishes a desired orientation of said display of said image signals;

wherein said image rotator comprises an image rotator processor for rotating the image represented by the image signals by an amount effectively determined by said rotation signal.

\* \* \* \* \*